United States Patent
Seki et al.

(10) Patent No.: US 7,528,602 B2
(45) Date of Patent: May 5, 2009

(54) MAGNETIC SHIELDING APPARATUS AND MAGNETIC FIELD MEASURING APPARATUS USING SAME

(75) Inventors: Yusuke Seki, Tokyo (JP); Mitsuru Onuma, Tokyo (JP); Akihiko Kandori, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 394 days.

(21) Appl. No.: 11/446,110

(22) Filed: Jun. 5, 2006

(65) Prior Publication Data

US 2007/0040554 A1   Feb. 22, 2007

(30) Foreign Application Priority Data

Jun. 10, 2005   (JP)  ............... 2005-170298

(51) Int. Cl.
   *G01V 3/00* (2006.01)
(52) U.S. Cl. ...................... 324/318; 324/320
(58) Field of Classification Search ............ 324/318, 324/301, 320
   See application file for complete search history.

(56) References Cited

U.S. PATENT DOCUMENTS

| | | | |
|---|---|---|---|
| 4,761,516 A | 8/1988 | Reichert | |
| 4,857,668 A | 8/1989 | Buonanno | |
| 6,528,994 B2 * | 3/2003 | Suzuki et al. | ............... 324/248 |
| 2002/0050815 A1 | 5/2002 | Suzuki et al. | |
| 2004/0106863 A1 | 6/2004 | Seki et al. | |

FOREIGN PATENT DOCUMENTS

| | | |
|---|---|---|
| EP | 1 634 531 A1 | 8/2005 |
| JP | 2002-136492 | 10/2000 |
| JP | 2006-75372 | 9/2004 |

* cited by examiner

*Primary Examiner*—Brij B. Shrivastav
*Assistant Examiner*—Megann E Vaughn
(74) *Attorney, Agent, or Firm*—Reed Smith LLP; Juan Carlos A. Marquez, Esq.

(57) ABSTRACT

A magnetic shielding apparatus having a high shielding effect. With the magnetic shielding apparatus having an opening (for example, a cylindrical magnetic shielding apparatus provided with a door), the door covering the opening is electrically and/or magnetically connected to a main body by means of electrically and/or magnetically connecting members. The magnetic shielding apparatus is higher in magnetic shielding factor than the conventional magnetic shielding apparatus, and a magnetic field measuring apparatus using the magnetic shielding apparatus, capable of measuring biomagnetism generated from an inspection target (a living body), with higher sensibility than before.

12 Claims, 18 Drawing Sheets

MAGNETIC SHIELDING APPARATUS AND MAGNETIC FIELD MEASURING APPARATUS USING SAME

CLAIM OF PRIORITY

The present application claims priority from Japanese application JP 2005-170298 filed on Jun. 10, 2005, the content of which is hereby incorporated by reference into this application.

CROSS-REFERENCE TO RELATED APPLICATION

This application is related to U.S. application Ser. No. 11/196,750 filed on Aug. 4, 2005, the disclosure of which is hereby incorporated by reference.

FIELD OF THE INVENTION

The present invention relates to a magnetic shielding apparatus for shielding ambient magnetic field noise, and a magnetic field measuring apparatus using the same.

BACKGROUND OF THE INVENTION

A conventional magnetic shielding apparatus for shielding an ambient magnetic field (external magnetic field), used in measurement of biomagnetism generated from a living body, has been built as a spatially closed chamber in a box-like shape, formed by tightening a sheet material high in permeability (a high-permeability material such as Permalloy, and so forth) up to a frame made of aluminum, and stainless steel, without any gap interjacent there between, by use of bolts or the like so as to be fixedly attached thereto. Further, a sheet material of Permalloy has been disposed in multiple layers to enhance a magnetic shielding factor, and a sheet material large in electric conductivity (aluminum, and so forth) has been used to shield electromagnetic waves. There has been reported a cylindrical magnetic shielding apparatus small in size and light in weight, using a high-permeability sheet material instead of Permalloy (refer to, for example, JP-A No. 136492/2002).

A high-permeability material generally refers to material having a relative magnetic permeability in a range of about 10,000 to 100,000. More specifically, Permalloy, silicon steel, and so forth are heavily used, and these materials are also called as a μ-metal. Those high-permeability materials have a property of allowing magnetic fluxes to easily penetrate there through, and this property is applied to magnetic shielding. For example, as shown in FIG. 18, when a cylinder 182 made of a high-permeability material is placed in an ambient magnetic field uniform in the vertical direction, lines of magnetic force 181 have distribution at a higher density within the high-permeability material than that in the air. As a result, a space loose in magnetic flux density occurs on the inner side of the cylinder 182, that is, there is formed a space that has shielded an external magnetic field. This is a fundamental principle behind magnetic shielding with the use of the high-permeability material.

Meanwhile, when an AC magnetic field is applied to an electrically conductive material such as metal, alloy, and so forth, a shielding current, so-called eddy current, is known to spontaneously occur within the material. The higher electric conductivity of the material, the greater an effect of the eddy current is, so that copper and aluminum are generally used as a magnetic shield. Further, it is known that the greater an area of a plane orthogonal to the direction of propagation of an electromagnetic wave, the greater the effect of the eddy current is.

Further, it is known that a magnetic shielding factor of the cylindrical magnetic shielding apparatus is higher in a direction orthogonal to a cylindrical axis than that in the direction of the cylindrical axis. Accordingly, in the case of carrying out measurement of a magnetic field inside the cylindrical magnetic shielding apparatus, a magnetic field component in the direction orthogonal to the cylindrical axis is measured more often than not. In the case of biomagnetism measurement for detecting a minute magnetism, use is generally made of a SQUID flux meter using a superconducting quantum interference device (SQUID). Further, there have been proposed two methods (refer to, for example, JP-A No. 136492/2002) for inserting an inspection target inside the cylindrical magnetic shielding apparatus, that is, (1) a method whereby the inspection target is inserted through open ends at respective ends of the cylindrical magnetic shielding apparatus, and (2) a method whereby the cylindrical magnetic shielding apparatus is provided with a door that can be opened and closed, and the inspection target is inserted through the door.

In general, the conventional cylindrical magnetic shielding apparatus in the form of a box-like chamber has a floor about 2 m in longitudinal as well as transverse dimension, and is about 2 m in height, weighing heavily, so that there has been a problem in that there are limitations to a room where the apparatus can be installed, and in addition, a cost thereof is high.

The method for inserting the inspection target inside the cylindrical magnetic shielding apparatus under (1) as above has an advantage in that since no door is installed, a structure becomes simpler, however, the method has had a problem in that an inspection engineer finds it difficult to observe the interior condition of the magnetic shielding apparatus, and to accurately adjust an inspection position. Furthermore, as there is a need for pulling out a bed in order to place the inspection target thereon, there is a need for preparing a room about 4 m in length in order to enable the magnetic shielding apparatus to be installed therein on the assumption that the magnetic shielding apparatus, in the direction of the cylindrical axis, is about 2 m in length.

SUMMARY OF THE INVENTION

With the method for inserting the inspection target inside the cylindrical magnetic shielding apparatus under (2) as above, since a door is installed, an inspection engineer can easily observe the interior condition of the magnetic shielding apparatus to thereby accurately adjust an inspection position. Further, since there is no need for pulling out the bed in the direction of the cylindrical axis, this method has an advantageous effect of reducing space required for the inspection. However, the conventional cylindrical magnetic shielding apparatus has had a problem that its shielding effect is insufficient owing to a gap existing between the door and a main body.

With a magnetic shielding apparatus having an opening (for example, a cylindrical magnetic shielding apparatus provided with a door) according to the invention, a door covering the opening is electrically and/or magnetically connected to a main body. By so doing, the problem described as above is resolved, and it is possible to provide a magnetic shielding apparatus having a magnetic shielding factor larger than that for the conventional magnetic shielding apparatus, and a magnetic field measuring apparatus using the same.

More specifically, the invention provides, for example, a magnetic shielding apparatus which includes first and second nonmagnetic cylindrical members having circumferential parts of first and second predetermined angular ranges, respectively, formed by disposing a plurality of high-permeability members having a high permeability so as to partially overlap each other, and to concentrically surround one axis; means for fixedly attaching the first cylindrical member to a floor surface substantially vertical to the one axis; and means for rotating the second cylindrical member around the one axis, and is characterized in that the first cylindrical member and the second cylindrical member overlap each other for a third predetermined angular range at respective ends thereof, in a direction parallel to the one axis, due to rotation of the second cylindrical member to thereby shield a component of an external magnetic filed, in a direction vertical to the one axis, to be split in two in the circumferential direction; and the first cylindrical member being in a state of being closed in the circumferential direction upon the first cylindrical member and the second cylindrical member overlapping each other for the third predetermined angular range, said magnetic shielding apparatus further comprising electrically and/or magnetically connecting members for electrically and/or magnetically connecting between respective portions of the first cylindrical member and the second cylindrical member, overlapping each other, upon the first cylindrical member being in the state of being closed.

For example, with a cylindrical magnetic shielding apparatus according to the invention, shown in FIGS. 1, and 10, an inner diameter thereof is about 1 m, and a length thereof, in an axial direction, is about 2 m by way of example. The cylindrical magnetic shielding apparatus is provided with a magnetic shielding cylinder 1001 having a first angular range in relation to the z-axis, and a rotatable door 1002 having a second angular range in relation to the z-axis. A magnetic shielding cylinder 1 is supported by shield supports 6a, 6b. The rotatable door 1002 is rotated along a circumferential part of the magnetic shielding cylinder 1001 in a circumferential direction of the z-axis by rotating parts 7a, 7b to thereby execute opening/closing of an opening 9 formed in the circumferential direction. With the cylindrical magnetic shielding apparatus, the circumferential part of the magnetic shielding cylinder 1001 is electrically and/or magnetically connected to the rotatable door 1002 when the opening 9 is closed by the rotatable door 1002, whereupon an inner space cylindrical in shape is formed, and an ambient magnetic field is prevented from intruding into the inner space. A component of a magnetic field generated from an inspection target brought into the inner space through the opening 9 formed in the circumferential direction when the rotatable door 1002 is opened, in the direction of the z-axis, is measured when the opening 9 is closed.

Further, the magnetic field measuring apparatus according to the invention comprises the magnetic shielding apparatus described as above, means for holding a living body with a direction of the body axis thereof, kept substantially parallel to the one axis inside the magnetic shielding apparatus, and a magneto metric sensor (for example, a SQUID flux meter) for detecting a component of a magnetic filed generated from the living body, in a direction vertical to the one axis.

The invention can provide the magnetic shielding apparatus higher in magnetic shielding factor than the conventional magnetic shielding apparatus, and a magnetic field measuring apparatus using the magnetic shielding apparatus, capable of measuring biomagnetism generated from an inspection target (a living body), with higher sensibility than before.

DETAILED DESCRIPTION OF THE PREFERRED EMBODIMENTS

Figure 1A:
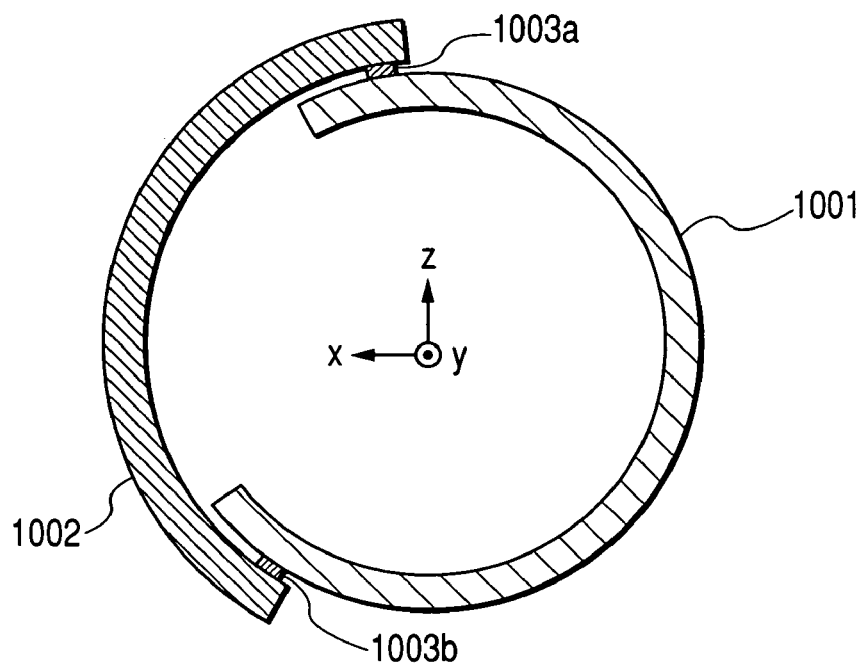
FIG. 1A is a cross-sectional view of an embodiment of a magnetic shielding apparatus according to the invention.

Embodiments of the invention are described hereinafter with reference to the accompanying drawings. In FIGS. 1 to 17, elements having like functions are denoted by like reference numerals. Further, in FIGS. 1 to 17, it is assumed that the origins (0, 0, 0) of Cartesian coordinate system (x, y, z) correspond to the center O of a magnetic shielding apparatus, the y-axis corresponds to the center axis (cylindrical axis) of the magnetic shielding apparatus, and an x-y plane corresponds to a detection plane (a plane along a detection coil) of a single, or a plurality of SQUID flux meters, that is, a plane parallel to a measurement plane. The SQUID flux meter detects a component of a magnetic field generated from an inspection target, in the direction of the z-axis.

In the Cartesian coordinate system (x, y, z) shown in FIGS. 1 to 17, respectively, if the origins (0, 0, 0) coincide with the center O of the magnetic shielding apparatus, the origin O is explicitly shown in those figures. The Cartesian coordinate system (x, y, z) where the origin O is not explicitly shown in those figures is one shown in as-translated state. Further, it is sufficient for the measurement plane of the single, or the plurality of the SQUID flux meters to be in close proximity to the center axis of the magnetic shielding apparatus, and the measurement plane may either coincide, or not coincide with the x-y plane of the magnetic shielding apparatus.

Figure 13:
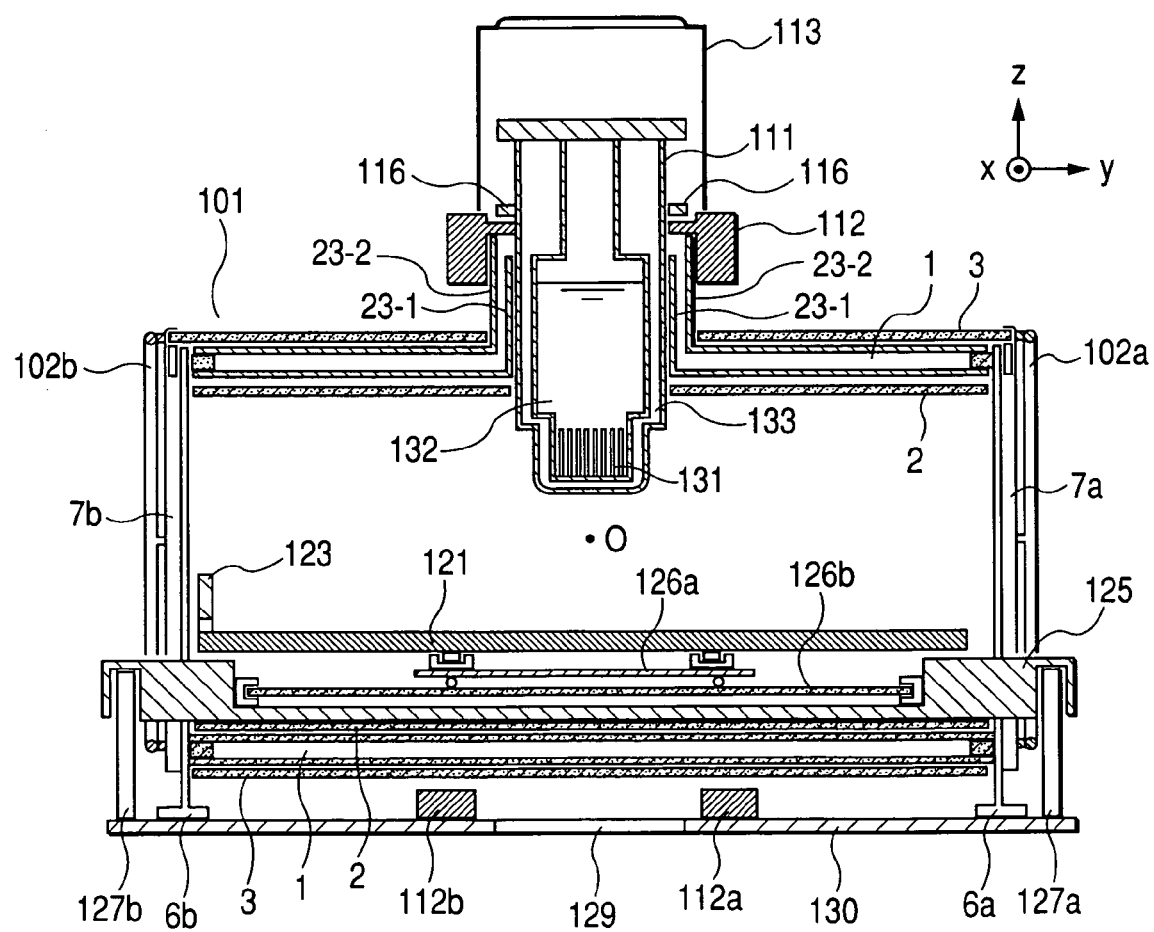
FIG. 13 is a sectional view of the biomagnetism measuring apparatus shown in FIG. 12, taken along a y-z plane.

Further, as shown in FIG. 13 referred to later in the present description, a SQUID flux meter 131 is cooled to a low temperature by the agency of liquid helium 132, and is thermally insulated from the outside through the intermediary of a vacuum layer 133. The SQUID flux meter 131 is inserted in the interior of a magnetic shielding apparatus 101. The closer to the center of the magnetic shielding apparatus 101 in the interior thereof, the smaller ambient magnetic field noise becomes, and the more uniform a magnetic field profile becomes, so that a detection coil (not shown) of the single, or the plurality of the SQUID flux meters 131 is preferably in close proximity to the center O of the magnetic shielding apparatus 101 {the origins (0, 0, 0) of the Cartesian coordinate system (x, y, z)}.

For apparatuses (magnetic shielding apparatuses, and biomagnetism measuring apparatuses using the same) according to embodiments of the invention, as described hereinafter, use can be made of Permalloy, silicon steel, and an amorphous material as a high-permeability material. For example, according to representative embodiments of the invention, a sheet material made of Permalloy, and so forth, or a sheet material made of an amorphous alloy, having a high relative magnetic permeability in a range of about 10,000 to 100,000, can used as the high-permeability material, and a sheet material made of aluminum, copper, and so forth, having a high electric conductivity, can be used as a highly electrically conductive material. Further, elements disposed inside the magnetic shielding apparatus, and in close proximity thereto, as explained with reference to the embodiments described hereinafter, are made of a nonmagnetic material {wood, and FRP (fiber-reinforced plastics)}, aluminum, SUS, and so forth. For a superconducting material making up the SQUID flux meter 131 that is used in the apparatuses according to the embodiments described hereinafter, use can be made of a low-temperature superconducting material having a low superconducting transition temperature, acting as a superconductor at a low temperature (for example, liquid helium temperature), or a high-temperature superconducting material having a high superconducting transition temperature, acting as a superconductor at a high temperature (for example, liquid nitrogen temperature). Furthermore, it is also possible to use a superconducting material having a superconducting transition temperature higher than the liquid nitrogen temperature as well as a superconducting material having a superconducting transition temperature between the liquid helium temperature, and the liquid nitrogen temperature.

Figure 1B:
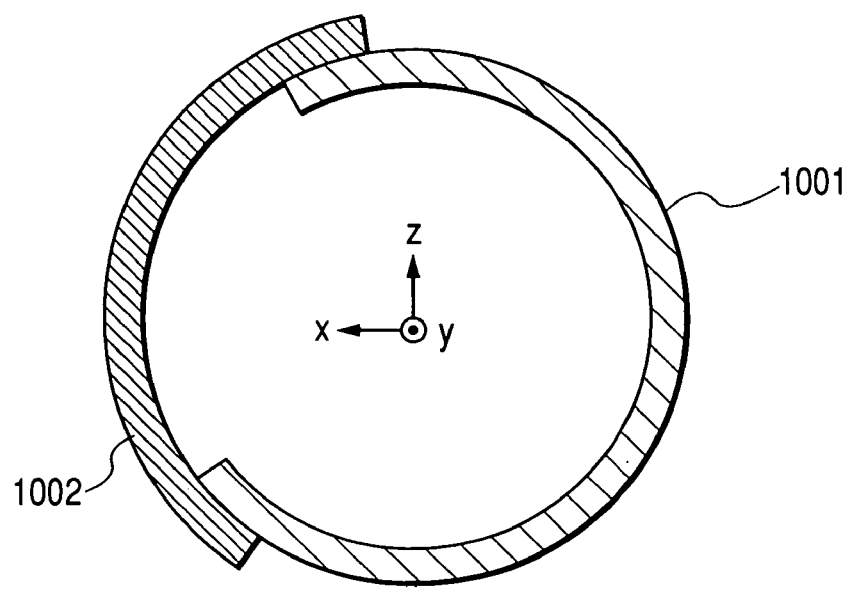
FIG. 1B is a cross-sectional view of another embodiment of a magnetic shielding apparatus according to the invention.

FIGS. 1A and 1B are cross-sectional views of a magnetic shielding apparatus according to one embodiment of the invention, showing that as a magnetic shielding door 1002 is shifted, an opening of a magnetic shielding cylinder 1001 is closed, and the magnetic shielding cylinder 1001, and the magnetic shielding door 1002 are electrically or magnetically connected to each other. FIG. 1A is a cross-sectional view showing electrical or magnetic connection between the magnetic shielding cylinder 1001, and the magnetic shielding door 1002, implemented through the intermediary of electromagnetic connecting members 1003a, 1003b. FIG. 1B is a cross-sectional view showing electrical or magnetic connection between the magnetic shielding cylinder 1001, and the magnetic shielding door 1002, implemented through direct contact there between.

The magnetic shielding apparatus shown in FIG. 1A comprises main members including the magnetic shielding cylinder 1001 disposed so as to surround the y-axis, the magnetic shielding door 1002, and the electromagnetic connecting members 1003a, 1003b, for electrically or magnetically connecting the magnetic shielding cylinder 1001 to the magnetic shielding door 1002. The magnetic shielding cylinder 1001 and the magnetic shielding door 1002 are each made of a high-permeability material, or a highly electrically conductive material. The electromagnetic connecting members 1003a, 1003b are each made of the high-permeability material, the highly electrically conductive material, or a combination thereof. As the magnetic shielding door 1002 is shifted, an opening of the magnetic shielding cylinder 1001 is closed, and the magnetic shielding cylinder 1001, and the magnetic shielding door 1002 are electrically or magnetically connected to each other through the intermediary of the electromagnetic connecting members 1003a, 1003b, thereby shielding a component of an external magnetic field, in the direction vertical to the y-axis. In FIG. 1A, the magnetic shielding door 1002 is disposed on the outer side of the magnetic shielding cylinder 1001, however, the magnetic shielding door 1002 may be disposed on the inner side of the magnetic shielding cylinder 1001.

The magnetic shielding apparatus shown in FIG. 1B comprises main members including the magnetic shielding cylinder 1001 disposed so as to surround the y-axis, and the magnetic shielding door 1002. The magnetic shielding cylinder 1001 and the magnetic shielding door 1002 are each made of a high-permeability material, or a highly electrically conductive material. As the magnetic shielding door 1002 is shifted, an opening of the magnetic shielding cylinder 1001 is closed, and the magnetic shielding cylinder 1001, and the magnetic shielding door 1002 are electrically or magnetically connected to each other through contact there between, thereby shielding the component of the external magnetic field, in the direction vertical to the y-axis. In FIG. 1B, the magnetic shielding door 1002 is disposed on the outer side of the magnetic shielding cylinder 1001; however, the magnetic shielding door 1002 may be disposed on the inner side of the magnetic shielding cylinder 1001.

In the case where the magnetic shielding cylinder 1001 is electrically connected to the magnetic shielding door 1002 as shown in FIGS. 1A and 1B, respectively, there is generated a shielding current throughout the magnetic shielding cylinder 1001 and the magnetic shielding door 1002, respectively, against a varying external magnetic field, thereby exhibiting an advantageous effect of the shielding current canceling out the external magnetic field. On the other hand, in the case where the magnetic shielding cylinder 1001 is not electrically connected to the magnetic shielding door 1002, paths over which the shielding current flows are cut off at boundaries between the magnetic shielding cylinder 1001 and the magnetic shielding door 1002, so that there occurs reduction in the advantageous effect of the shielding current. Accordingly, by electrically connecting the magnetic shielding cylinder 1001 to the magnetic shielding door 1002 with adoption of makeup shown in FIG. 1A or 1B, a magnetic shielding effect of the magnetic shielding apparatus is enhanced.

Figure 18:
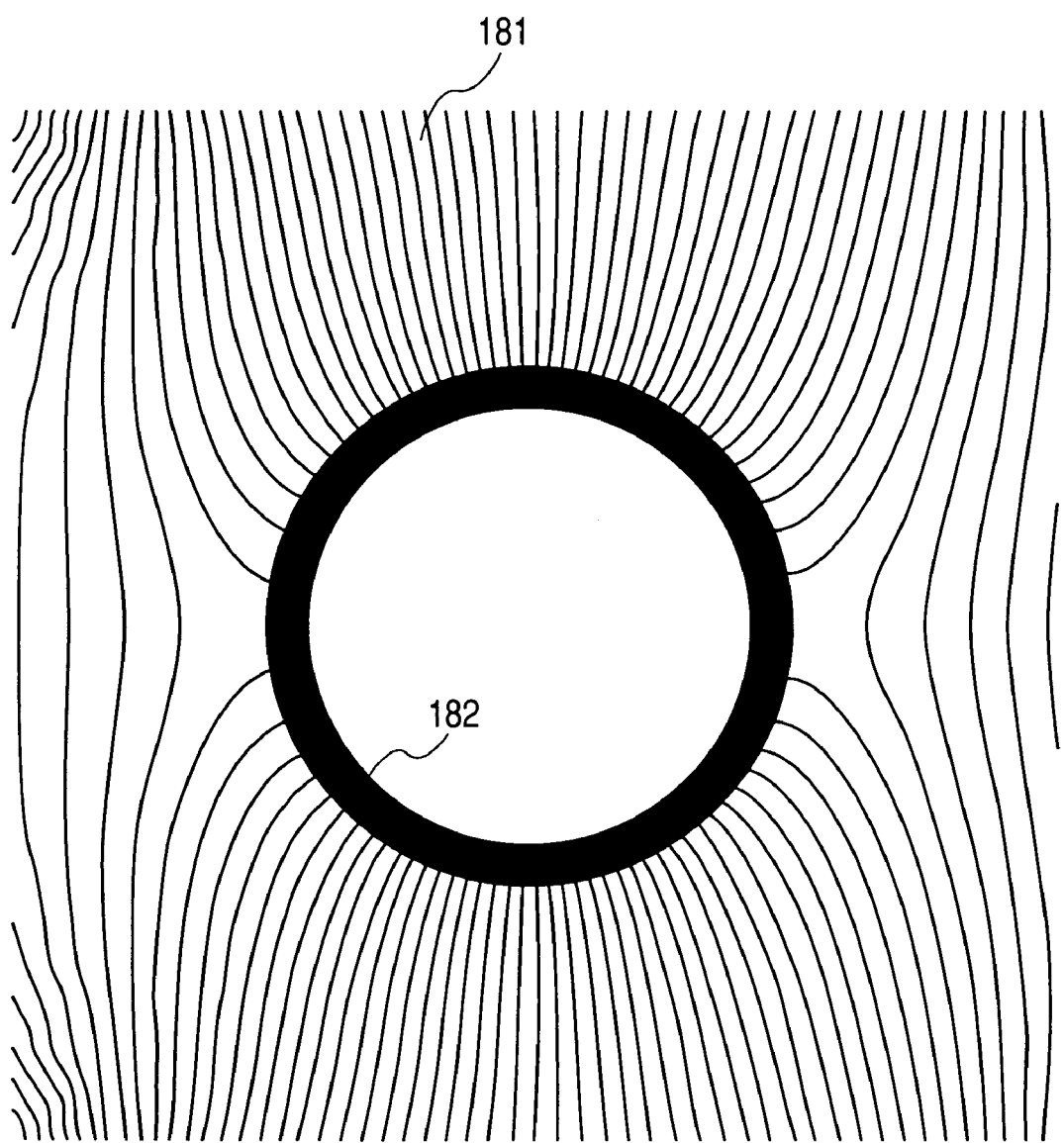
FIG. 18 is a schematic illustration showing distribution of lines of magnetic force when a cylinder 182 made of a high-permeability material is placed in an ambient magnetic field uniform in the vertical direction.

Further, in the case where the magnetic shielding cylinder 1001 is magnetically connected to the magnetic shielding door 1002, as shown in FIGS. 1A and 1B, respectively, magnetic flux lines of the external magnetic field are formed to have such a distribution as shown in FIG. 18, hardly intruding into an inner space enclosed by the magnetic shielding cylinder 1001 and the magnetic shielding door 1002, so that the magnetic shielding apparatuses shown in FIGS. 1A and 1B, respectively, can achieve a high magnetic shielding effect. On the other hand, in the case where the magnetic shielding cylinder 1001 is not magnetically connected to the magnetic shielding door 1002, paths of magnetic fluxes are cut off at the boundaries between the magnetic shielding cylinder 1001 and the magnetic shielding door 1002, so that the magnetic flux lines intrude into the inner space through gaps between the magnetic shielding cylinder 1001 and the magnetic shielding door 1002, resulting in reduction of the magnetic shielding effect. Accordingly, by magnetically connecting the magnetic shielding cylinder 1001 to the magnetic shielding door 1002 with the adoption of the makeup shown in FIG. 1A or 1B, the magnetic shielding effect of the magnetic shielding apparatus can be enhanced.

With the cylindrical magnetic shielding apparatus according to the invention, in particular, as a wide opening can be set by shifting a rotatable door in the circumferential direction while openings are provided in the forward and backward directions along the y-axis, respectively, the apparatus is excellent in openness, and workability in positioning of a patient, conducted by a doctor or an inspection engineer as well as operability, so that it is possible to relieve a patient from feeling of oppression, or insecure feeling, due to the patient being placed in a narrow enclosed space.

Figure 2A:
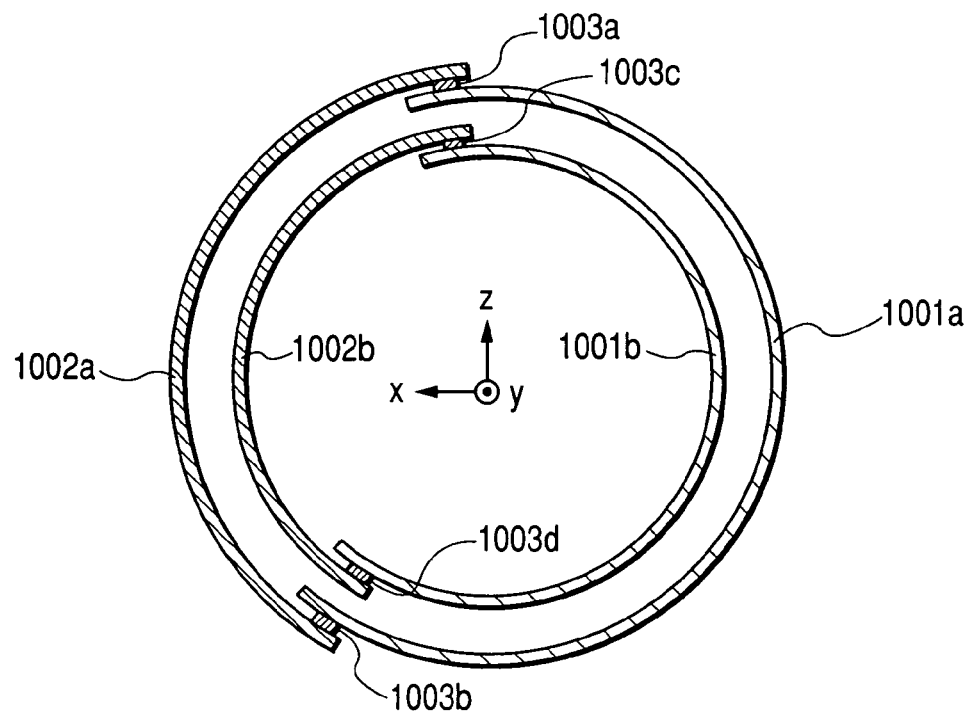
FIG. 2A is a cross-sectional view of still another embodiment of a magnetic shielding apparatus according to the invention.
Figure 2B:
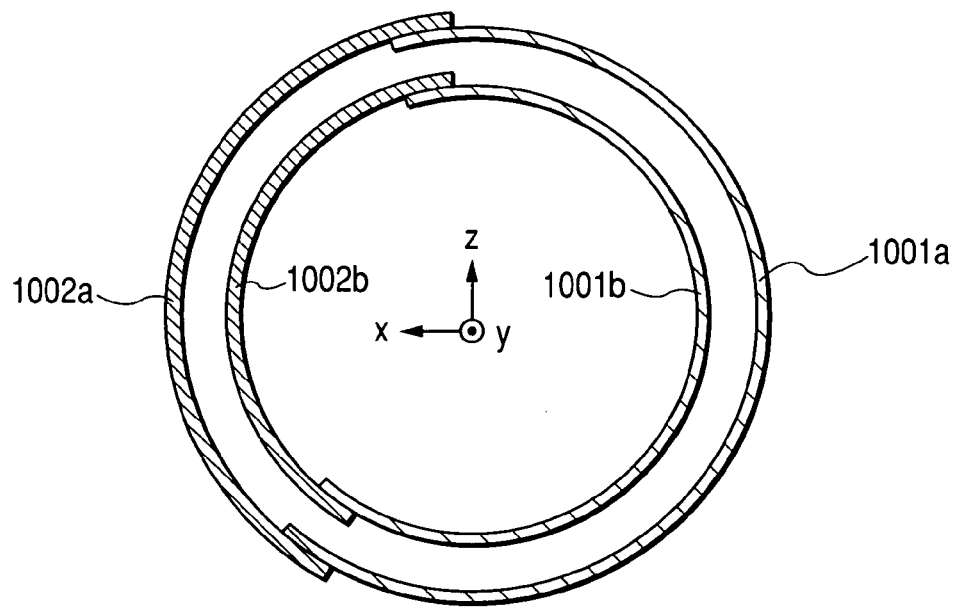
FIG. 2B is a cross-sectional view of a further embodiment of a magnetic shielding apparatus according to the invention.

FIGS. 2A and 2B are cross-sectional views of another embodiment of a magnetic shielding apparatus according to the invention, wherein the magnetic shielding cylinder 1001, and the magnetic shielding door 1002, shown in FIG. 1, are each disposed so as to form a dual structure. By disposing the magnetic shielding cylinder 1001, and the magnetic shielding door 1002 so as to form a multi-layer structure, respectively, as shown in FIGS. 2A and 2B, the magnetic shielding effect of the magnetic shielding apparatus can be enhanced.

The magnetic shielding apparatus shown in FIG. 2A comprises main members including magnetic shielding cylinders 1001a, 100b, disposed so as to surround the y-axis, magnetic shielding doors 1002a, 1002b, electromagnetic connecting members 1003a, 1003b, for electrically or magnetically connecting the magnetic shielding cylinder 1001a to the magnetic shielding door 1002a, and the electromagnetic connecting members 1003c, 1003d for electrically or magnetically connecting the magnetic shielding cylinder 1001b to the magnetic shielding door 1002b. The magnetic shielding cylinders 1001a, 1001b, and the magnetic shielding door 1002a, 1002b are each made of the high-permeability material, or the highly electrically conductive material. The electromagnetic connecting members 1003a, 1003b, 1003c, 1003d are each made of the high-permeability material, the highly electrically conductive material, or a combination thereof. As the magnetic shielding doors 1002a, 11002b are shifted, respective openings of the magnetic shielding cylinder 1001a, 1001b are closed, and the magnetic shielding cylinder 1001a, and the magnetic shielding door 1002a are electrically or magnetically connected to each other through the intermediary of electromagnetic connecting members 1003a, 1003b, respectively, while the magnetic shielding cylinder 100b, and the magnetic shielding door 1002b are electrically or magnetically connected to each other through the intermediary of electromagnetic connecting members 1003c, 1003d, respectively, whereupon a component of an external magnetic field, in the direction vertical to the y-axis, is shielded. In FIG. 2A, the magnetic shielding door 1002a is disposed on the outer side of the magnetic shielding cylinder 1001a, however, the magnetic shielding door 1002a may be disposed on the inner side of the magnetic shielding cylinder 1001a. Further, the magnetic shielding door 1002b is disposed on the outer side of the magnetic shielding cylinder 1001b, however, the magnetic shielding door 1002b may be disposed on the inner side of the magnetic shielding cylinder 1001b.

The magnetic shielding apparatus shown in FIG. 2B comprises main members including magnetic shielding cylinders 1001a, 1001b, disposed so as to surround the y-axis, and magnetic shielding doors 1002a, 1002b. The magnetic shielding cylinders 1001a, 1001b, and the magnetic shielding door 1002a, 1002b are each made of the high-permeability material, or the highly electrically conductive material. As the magnetic shielding doors 1002a, 11002b are shifted, respective openings of the magnetic shielding cylinder 1001a, 1001b are closed, whereupon the magnetic shielding cylinder 1001a, and the magnetic shielding door 1002a are electrically or magnetically connected to each other through contact there between, and magnetic shielding cylinder 100b, and the magnetic shielding door 1002b are electrically or magnetically connected to each other through contact there between, thereby shielding a component of the external magnetic field, in the direction vertical to the y-axis. In FIG. 2A, the magnetic shielding door 1002a is disposed on the outer side of the magnetic shielding cylinder 1001a, however, the magnetic shielding door 1002a may be disposed on the inner side of the magnetic shielding cylinder 1001a. Further, the magnetic shielding door 1002b is disposed on the outer side of the magnetic shielding cylinder 1001b, however, the magnetic shielding door 1002b may be disposed on the inner side of the magnetic shielding cylinder 1001b.

Figure 3A:
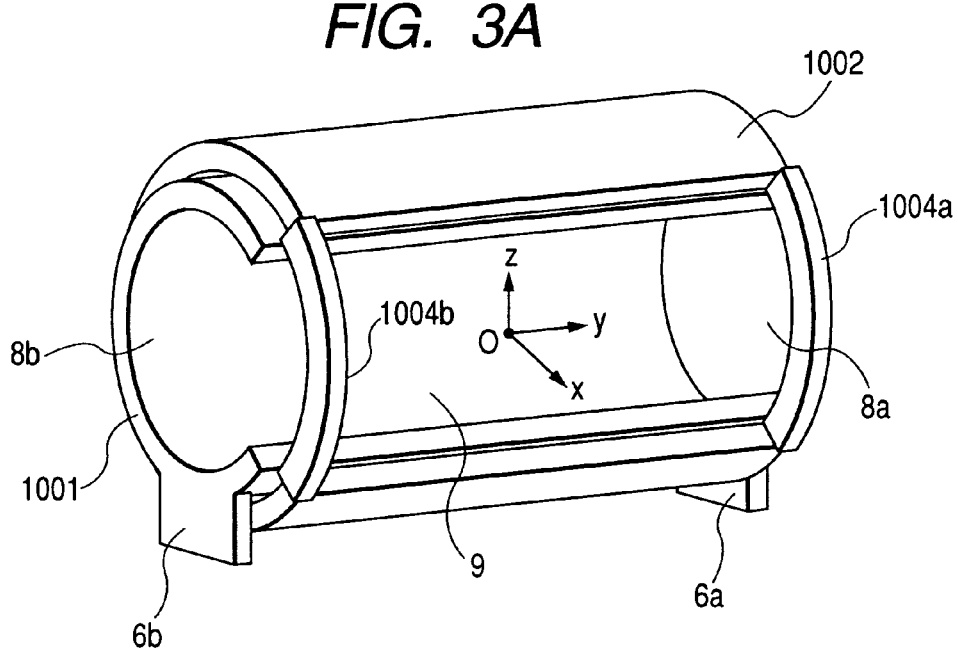
FIG. 3A is a perspective view of a still further embodiment of a magnetic shielding apparatus according to the invention.
Figure 3B:
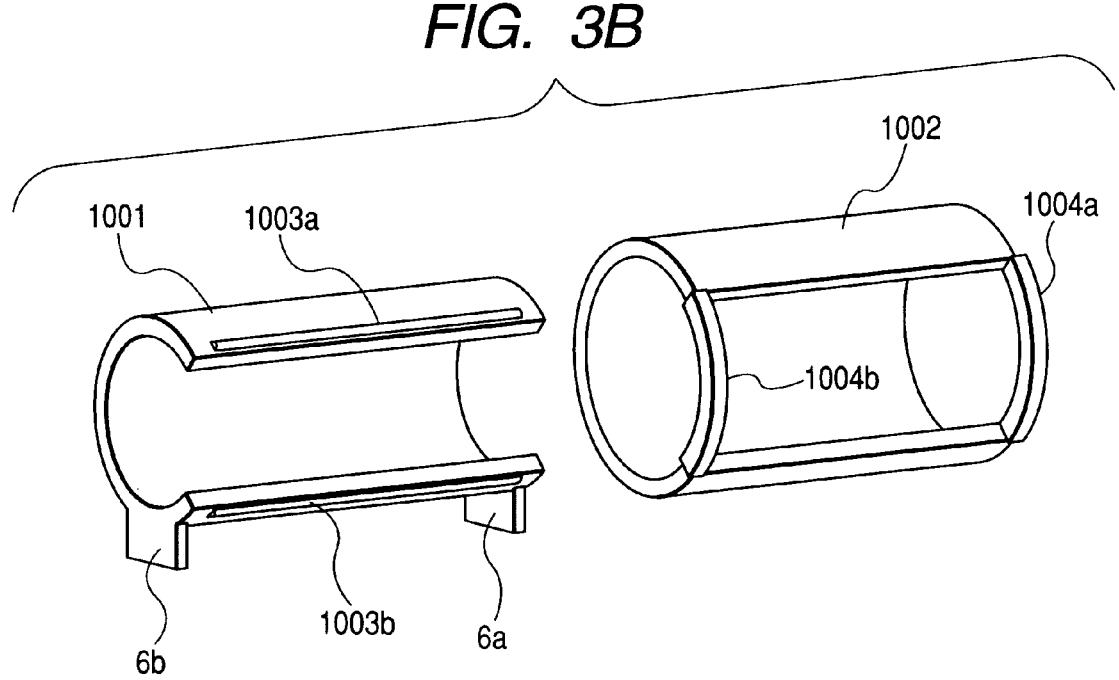
FIG. 3B is an assembly view of the magnetic shielding apparatus shown in FIG. 3A.
Figure 4A:
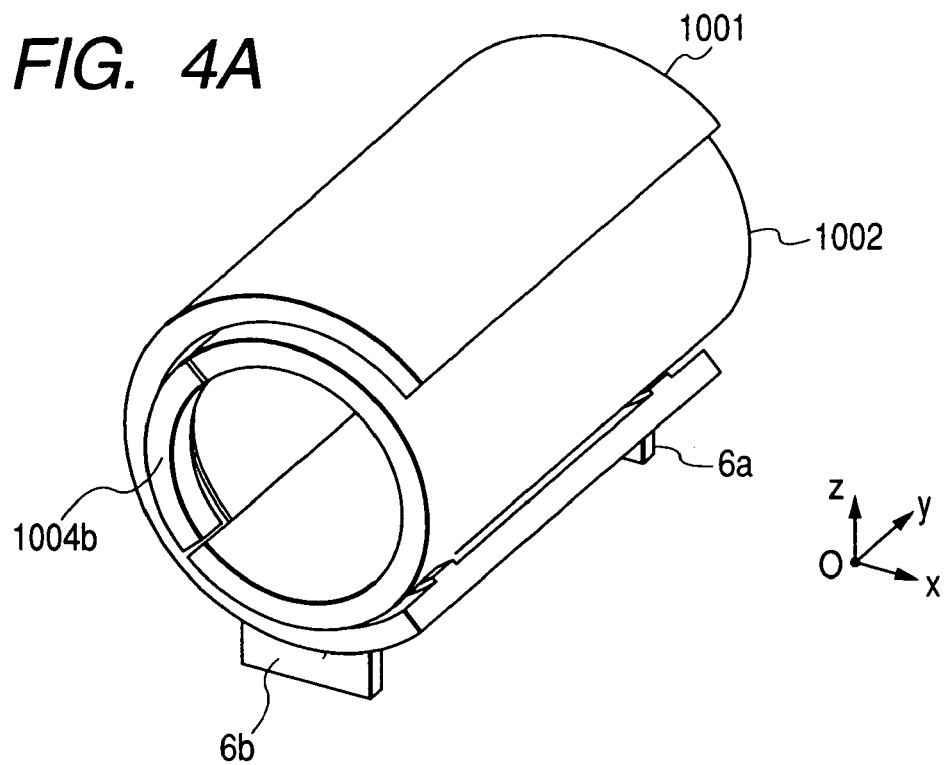
FIG. 4A is a perspective view of a yet further embodiment of a magnetic shielding apparatus according to the invention.

FIGS. 3A, 3B, 4A, and 4B are views of magnetic shielding apparatuses according to other embodiments of the invention, respectively. FIG. 3A is a perspective view of the magnetic shielding apparatus wherein a magnetic shielding door 1002 is disposed on the outer side of a magnetic shielding cylinder 1001, showing the magnetic shielding door 1002 in as-opened state. FIG. 4A is a perspective view of the magnetic shielding apparatus wherein a magnetic shielding door 1002 is disposed on the inner side of a magnetic shielding cylinder 1001, showing the magnetic shielding door 1002 in as-closed state.

The magnetic shielding apparatuses shown FIGS. 3A and 4A, respectively, comprise main members including the magnetic shielding cylinder 1001 disposed so as to surround the y-axis, the magnetic shielding door 1002, and electromagnetic connecting members 1003a, 1003b, for electrically or magnetically connecting the magnetic shielding cylinder 1001 to the magnetic shielding door 1002. Openings 8a, 8b are provided at respective ends of the magnetic shielding apparatus, in the direction of the y-axis.

The magnetic shielding cylinder 1001 and the magnetic shielding door 1002 are each made of the high-permeability material, or the highly electrically conductive material. The electromagnetic connecting members 1003a, 1003b are each made of the high-permeability material, the highly electrically conductive material, or a combination thereof. The magnetic shielding cylinder 1001 is joined to, and supported by shield supports 6a, 6b. The shield supports 6a, 6b are either fixedly attached to a floor, or fixedly attached to a metal plate disposed on the floor so as to enable pressure to be dispersed.

The magnetic shielding door 1002 is shifted upon its rotation around the y-axis. An opening 9 is provided at a side of the magnetic shielding cylinder 1001, and the opening 9 is closed or opened as the magnetic shielding door 1002 is shifted. Balancers 1004a, 1004b are disposed at the respective ends of the magnetic shielding door 1002 in order to facilitate shifting of the magnetic shielding door 1002. Respective weights and positions of the balancers 1004a, 1004b are preferably determined on conditions that balance is achieved between moment of inertia of the balancers 1004a, 1004b and moment of inertia of the magnetic shielding door 1002. More specifically, the magnetic shielding door 1002 preferably comes to a standstill at any position in a state of no external force being at work.

In FIGS. 3A and 4A, the magnetic shielding cylinder 1001, and the magnetic shielding door 1002 each are of a single-layer structure as with those shown in FIG. 1A; however, the magnetic shielding cylinder 1001, and the magnetic shielding door 1002 each may be formed so as to be of such a dual structure as shown in FIG. 2A. The magnetic field shielding performance of the magnetic shielding apparatus is enhanced by disposing the magnetic shielding cylinder 1001, and the magnetic shielding door 1002 so as to form a multi-layer structure, respectively.

Figure 4B:
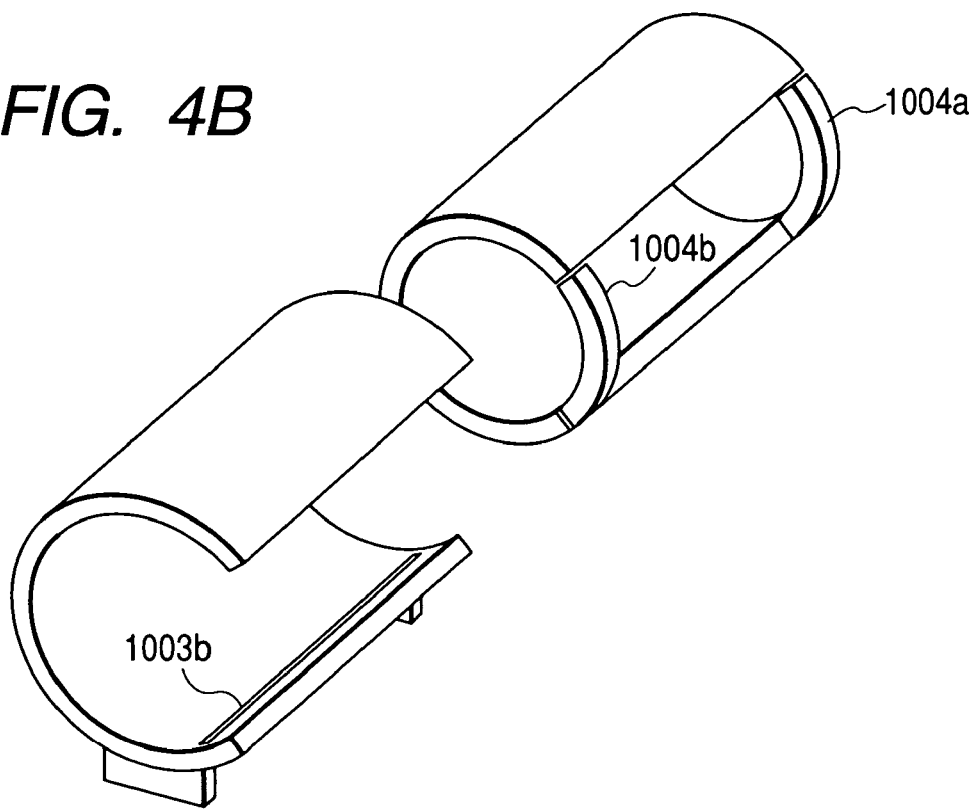
FIG. 4B is an assembly view of the magnetic shielding apparatus shown in FIG. 4A.

FIGS. 3B and 4B are perspective views showing makeup's of the magnetic shielding apparatuses shown in FIGS. 3A and 4A, respectively. The electromagnetic connecting members 1003a, 1003b are fixedly attached to a side face of the magnetic shielding cylinder 1001, respectively, to be electrically or magnetically connected thereto. The electromagnetic connecting members 1003a, 1003b are fixedly attached to respective regions where the magnetic shielding cylinder 1001 and the magnetic shielding door 1002 overlap each other so as to be electrically or magnetically connected to the magnetic shielding door 1002 in as-closed state. The electromagnetic connecting members 1003a, 1003b are preferably brought into intimate contact with the magnetic shielding door 1002 in order to enhance an effect of electrical or magnetic connection there between. Further, in order to improve adhesive properties of the electromagnetic connecting members 1003a, 1003b with the magnetic shielding door 1002, the electromagnetic connecting members 1003a, 1003b preferably have flexibility. FIGS. 3B and 4B, the electromagnetic connecting members 1003a, 1003b are fixedly attached to the side face of the magnetic shielding cylinder 1001, respectively, however, the electromagnetic connecting members 1003a, 1003b may be fixedly attached to a side face of the magnetic shielding door 1002 instead.

Figure 5A:
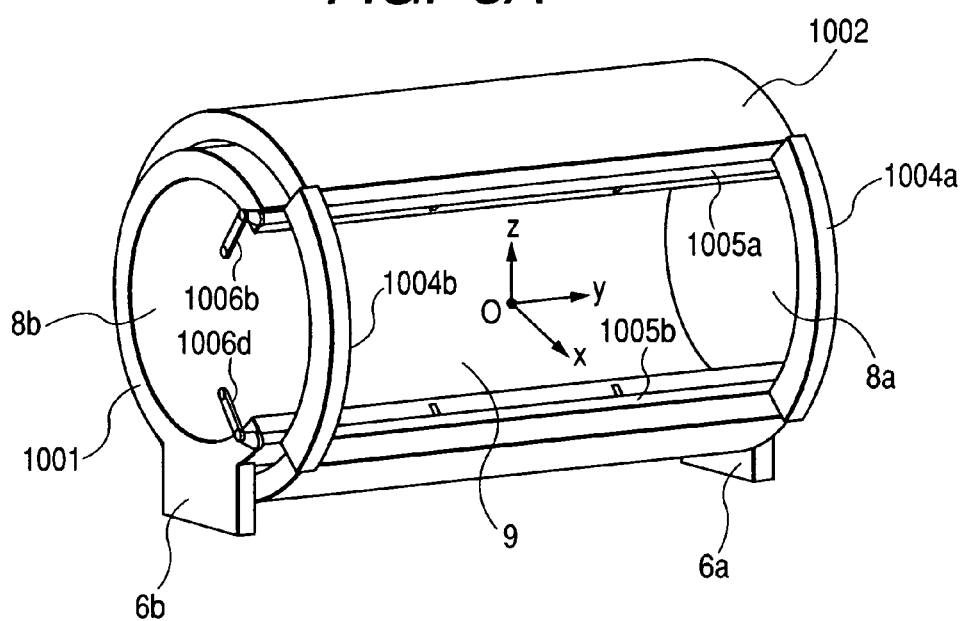
FIG. 5A is a perspective view of another embodiment of a magnetic shielding apparatus according to the invention.
Figure 5B:
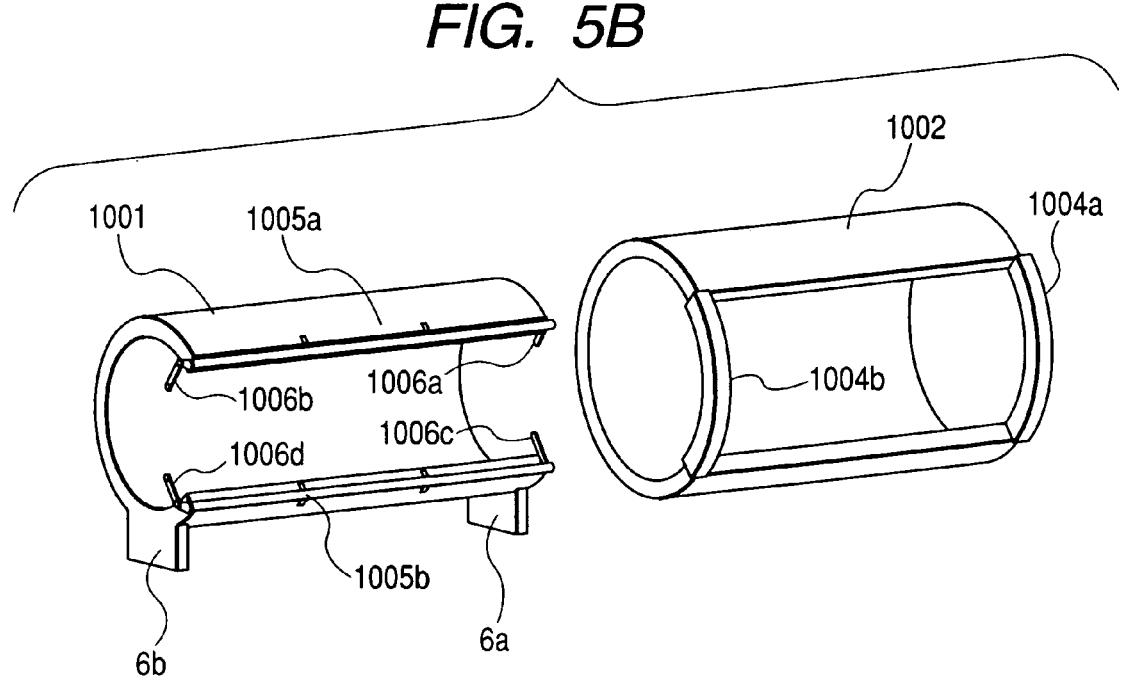
FIG. 5B is an assembly view of the magnetic shielding apparatus shown in FIG. 5A.

FIGS. 5A and 5B are perspective views of a magnetic shielding apparatus according to another embodiment of the invention. FIG. 5A is a perspective view of the magnetic shielding apparatus wherein a magnetic shielding door 1002 is disposed on the outer side of a magnetic shielding cylinder 1001, showing the magnetic shielding door 1002 in as-opened state. The magnetic shielding apparatus shown in FIG. 5A comprises main members including the magnetic shielding cylinder 1001 disposed so as to surround the y-axis, the magnetic shielding door 1002, and electromagnetic connecting members 1005a, 1005b, for electrically or magnetically connecting the magnetic shielding cylinder 1001 to the magnetic shielding door 1002. Openings 8a, 8b are provided at respective ends of the magnetic shielding apparatus, in the direction of the y-axis.

The magnetic shielding cylinder 1001 and the magnetic shielding door 1002 are each made of the high-permeability material, or the highly electrically conductive material. The electromagnetic connecting members 1005a, 1005b are each made of the high-permeability material, the highly electrically conductive material, or a combination thereof. The magnetic shielding cylinder 1001 is joined to, and supported by shield supports 6a, 6b.

The magnetic shielding door 1002 is shifted upon its rotation around the y-axis. An opening 9 is provided at a side of the magnetic shielding cylinder 1001, and the opening 9 is closed or opened as the magnetic shielding door 1002 is shifted. Balancers 1004a, 1004b are disposed at the respective ends of the magnetic shielding door 1002 in order to facilitate shifting of the magnetic shielding door 1002. Respective weights and positions of the balancers 1004a, 1004b are preferably determined on conditions that balance is achieved between moment of inertia of the balancers 1004a, 1004b and moment of inertia of the magnetic shielding door 1002. More specifically, the magnetic shielding door 1002 preferably comes to a standstill at any position in a state of no external force being at work.

In FIG. 5A, the magnetic shielding cylinder 1001, and the magnetic shielding door 1002 each are of a single-layer structure as with those shown in FIG. 1A; however, the magnetic shielding cylinder 1001, and the magnetic shielding door 1002 each may be formed so as to be of such a dual structure as shown in FIG. 2A. The magnetic field shielding performance of the magnetic shielding apparatus is enhanced by disposing the magnetic shielding cylinder 1001, and the magnetic shielding door 1002 so as to form a multi-layer structure, respectively. Further, in FIG. 5A, the magnetic shielding door 1002 is disposed on the outer side of the magnetic shielding cylinder 1001, however, the magnetic shielding door 1002 may be disposed on the inner side of the magnetic shielding cylinder 1001.

FIG. 5B is a perspective view showing a makeup of the magnetic shielding apparatus shown in FIG. 5A. With the magnetic shielding door 1002 kept in as-closed state, the electromagnetic connecting member 1005a is brought into contact with both the magnetic shielding cylinder 1001, and the magnetic shielding door 1002 by use of handles 1006a, 1006b, fixedly attached to the magnetic shielding cylinder 1001, to thereby electrically or magnetically connecting the magnetic shielding cylinder 1001 to the magnetic shielding door 1002. Similarly, the electromagnetic connecting member 1005b is brought into contact with both the magnetic shielding cylinder 1001, and the magnetic shielding door 1002 by use of handles 1006c, 1006d, fixedly attached to the magnetic shielding cylinder 1001, to thereby electrically or magnetically connecting the magnetic shielding cylinder 1001 to the magnetic shielding door 1002. By electrically or magnetically connecting the magnetic shielding cylinder 1001 to the magnetic shielding door 1002, it is possible to shield the component of the external magnetic field, in the direction vertical to the y-axis. In FIGS. 5A and 5B, the electromagnetic connecting members 1005a, 1005b, and the handles 1006a, 1006b, 1006c, 1006d are fixedly attached to the magnetic shielding cylinder 1001, respectively; however, the same may be fixedly attached to the magnetic shielding door 1002 instead of the magnetic shielding cylinder 1001.

Figure 6:
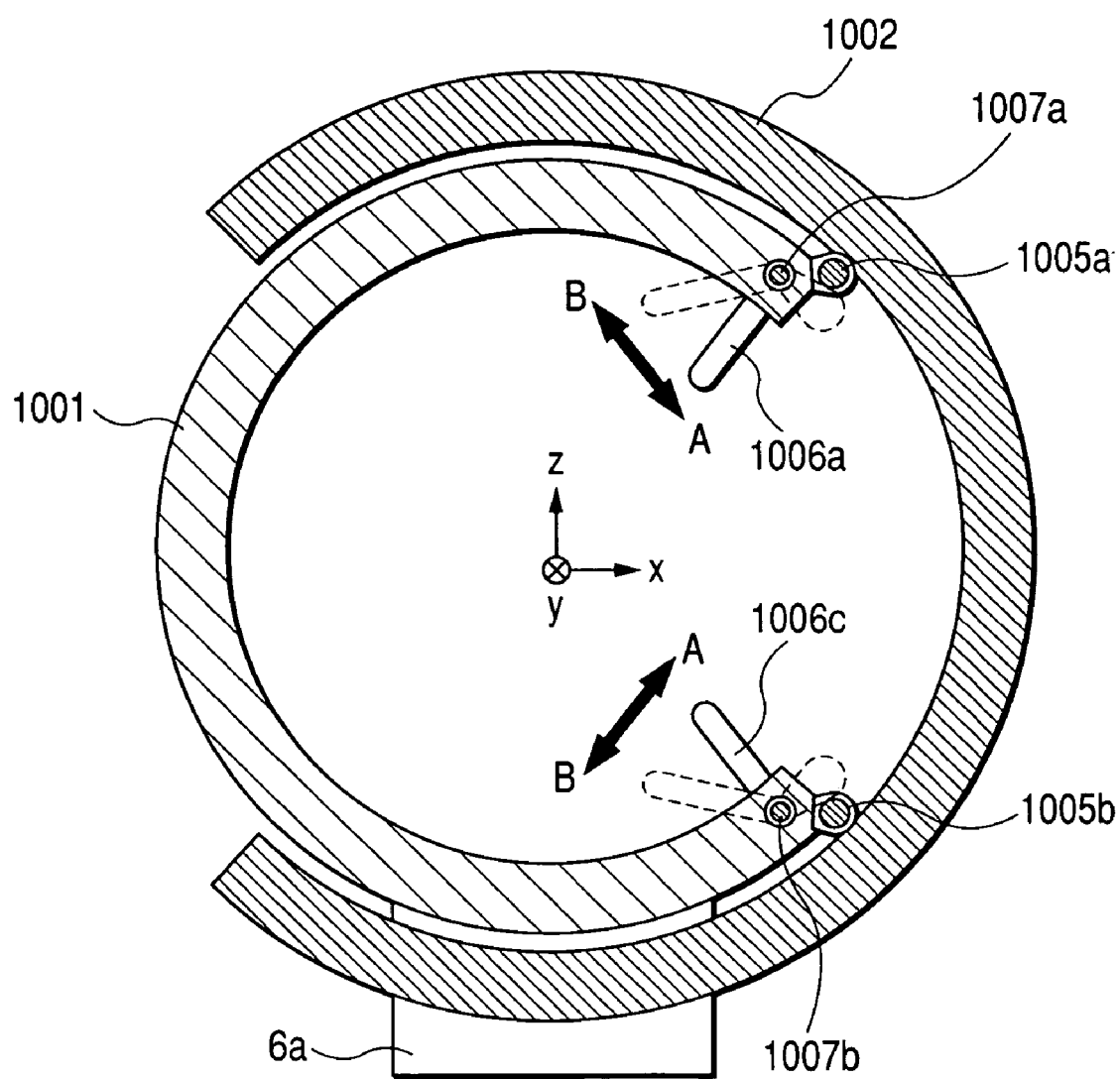
FIG. 6 is a cross-sectional view of the magnetic shielding apparatus in FIG. 5A.

FIG. 6 is a cross-sectional view of the magnetic shielding apparatus in FIGS. 5A and 5B, with the magnetic shielding door 1002 in a closed state, taken along an x-z plane. When the handle 1006a is thrown in the direction toward A with the magnetic shielding door 1002 kept in as-closed state, the electromagnetic connecting member 1005a is rotated around a fulcrum 1007a to be inserted into a gap between the magnetic shielding cylinder 1001, and the magnetic shielding door 1002, so that the magnetic shielding cylinder 1001, and the magnetic shielding door 1002 are electrically or magnetically connected to each other through the intermediary of the electromagnetic connecting member 1005a. On the contrary, when the handle 1006a is thrown in the direction toward B, the electromagnetic connecting member 1005a is rotated around the fulcrum 1007a to be taken out of the gap between the magnetic shielding cylinder 1001, and the magnetic shielding door 1002, so that the magnetic shielding cylinder 1001, and the magnetic shielding door 1002 are disengaged from electrical or magnetic connection there between.

Similarly, when the handle 1006b is thrown in the direction toward A, the electromagnetic connecting member 1005b is rotated around a fulcrum 1007b to be inserted into the gap between the magnetic shielding cylinder 1001, and the magnetic shielding door 1002, so that the magnetic shielding cylinder 1001, and the magnetic shielding door 1002 are electrically or magnetically connected to each other through the intermediary of the electromagnetic connecting member 1005b. When the handle 1006a is thrown in the direction toward B, the electromagnetic connecting member 1005a is rotated around the fulcrum 1007a to be taken out of the gap between the magnetic shielding cylinder 1001, and the magnetic shielding door 1002, so that the magnetic shielding cylinder 1001, and the magnetic shielding door 1002 are disengaged from electrical or magnetic connection there between.

Figure 7A:
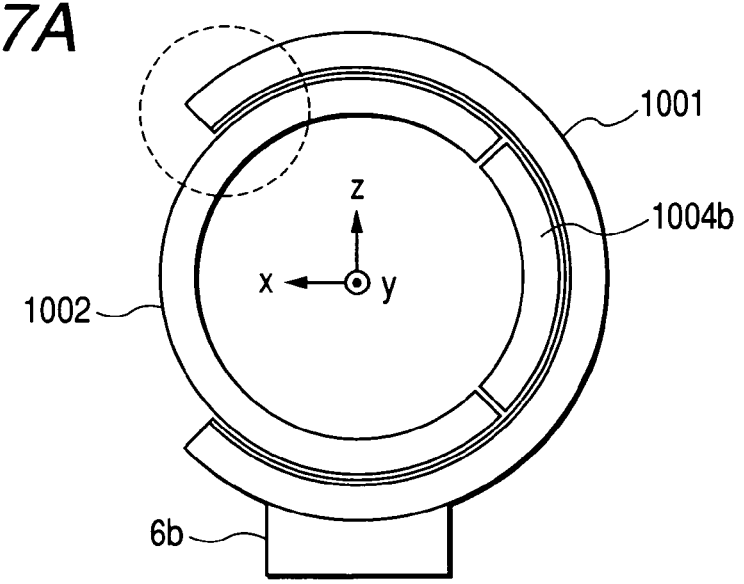
FIG. 7A is a cross-sectional view of the magnetic shielding apparatus according to one of the embodiments of the invention, FIGS. 7B and 7C being enlarged views of a region in FIG. 7A.
Figure 7B:
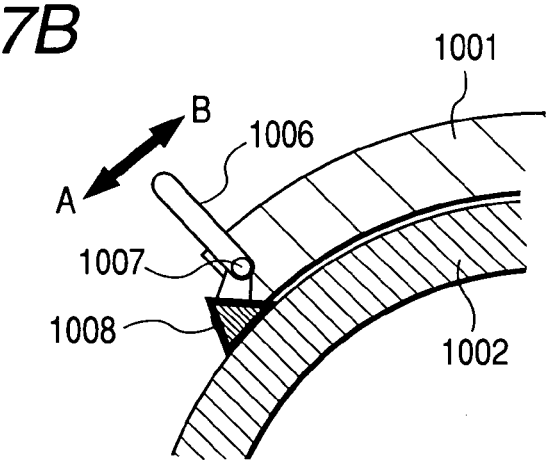
Figure 7C:
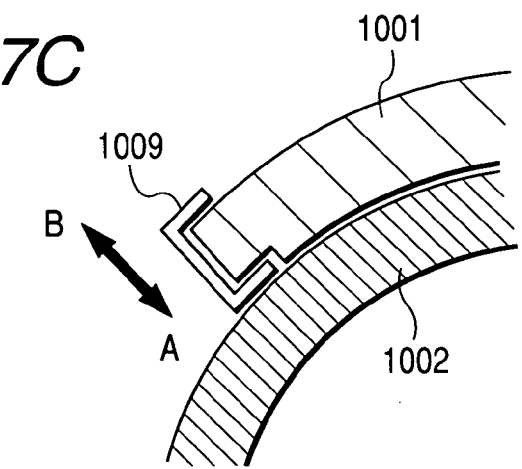

FIGS. 7A to 7C are cross-sectional views of the magnetic shielding apparatus according to one of the embodiments of the invention. FIG. 7A is a cross-sectional view of the magnetic shielding apparatus wherein the magnetic shielding door 1002 is disposed on the inner side of a magnetic shielding cylinder 1001, showing the magnetic shielding door 1002 in as-closed state. FIGS. 7B and 7C are enlarged views of a region in FIG. 7A, surrounded by a dotted line, each being a detailed view showing a method for electrical or magnetic connection between the magnetic shielding cylinder 1001, and the magnetic shielding door 1002.

With the method shown in FIG. 7B, when a handle 1006 is thrown in the direction toward A, a wedge-shaped electromagnetic connecting member 1008 is rotated around a fulcrum 1007 to be inserted into a gap between the magnetic shielding cylinder 1001, and the magnetic shielding door 1002, so that the magnetic shielding cylinder 1001, and the magnetic shielding door 1002 are electrically or magnetically connected to each other through the intermediary of the wedge-shaped electromagnetic connecting member 1008, thereby shielding a component of the external magnetic field, in the direction vertical to the y-axis. On the contrary, when the handle 1006 is thrown in the direction toward B, the wedge-shaped electromagnetic connecting member 1008 is rotated around the fulcrum 1007 to be taken out of the gap between the magnetic shielding cylinder 1001, and the magnetic shielding door 1002, so that the magnetic shielding cylinder 1001, and the magnetic shielding door 1002 are disengaged from electrical or magnetic connection there between. By use of the wedge-shaped electromagnetic connecting member 1008, as shown in FIG. 7B, it becomes possible to increase an area of contact between the wedge-shaped electromagnetic connecting member 1008 and the magnetic shielding cylinder 1001 as well as the magnetic shielding door 1002, so that electrical or magnetic connect ability between the magnetic shielding cylinder 1001, and the magnetic shielding door 1002 is enhanced.

With the method shown in FIG. 7C, when a sliding electromagnetic connecting member 1009 is caused to slide in the direction toward A, the sliding electromagnetic connecting member 1009 comes into contact with both the magnetic shielding cylinder 1001, and the magnetic shielding door 1002, so that the magnetic shielding cylinder 1001, and the magnetic shielding door 1002 are electrically or magnetically connected to each other through the intermediary of the sliding electromagnetic connecting member 1009, thereby shielding the component of the external magnetic field, in the direction vertical to the y-axis. On the contrary, when the sliding electromagnetic connecting member 1009 is caused to slide in the direction toward B, the sliding electromagnetic connecting member 1009 parts from the magnetic shielding door 1002, so that the magnetic shielding cylinder 1001, and the magnetic shielding door 1002 are disengaged from electrical or magnetic connection there between. With the method shown in FIG. 7C as well, an area of contact between the sliding electromagnetic connecting member 1009 and the magnetic shielding cylinder 1001 as well as the magnetic shielding door 1002, so that electrical or magnetic connect ability between the magnetic shielding cylinder 1001, and the magnetic shielding door 1002 can be enhanced.

Figure 8:
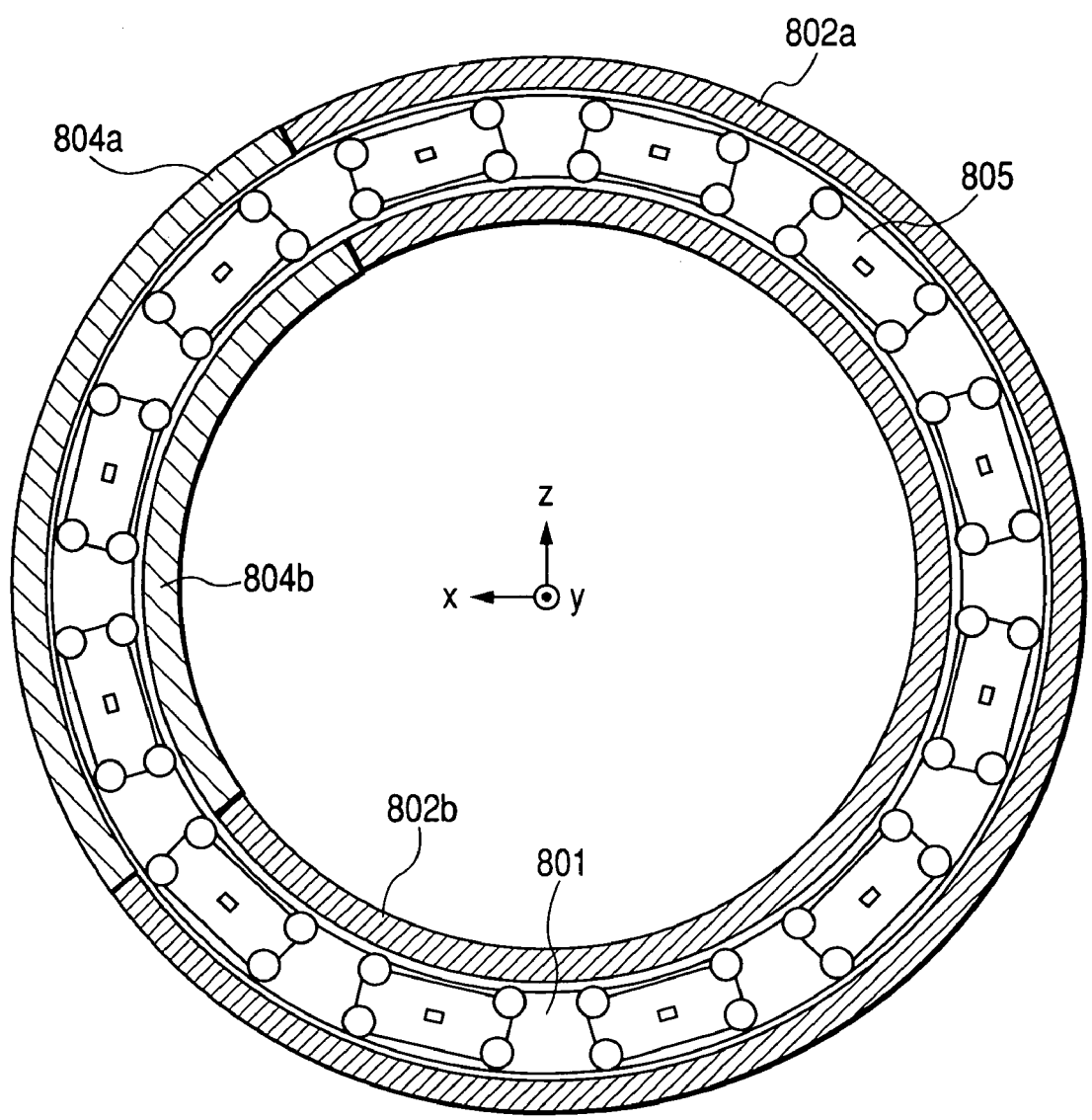
FIG. 8 is a cross-sectional view of a magnetic shielding apparatus according to another embodiment of the invention.

FIG. 8 is a cross-sectional view showing a shift mechanism of magnetic shielding doors of a magnetic shielding apparatus according to another embodiment of the invention. With the magnetic shielding apparatus shown in FIG. 8, a magnetic shielding door 802a is disposed on the outer side of a magnetic shielding cylinder 801 while a magnetic shielding door 802b is disposed on the inner side of the magnetic shielding cylinder 801. In FIG. 8, a roller assembly 805 substantially in the shape of a rectangle has a structure where a wheel is provided at four corners of the rectangle, and the roller assemblies 805 are disposed at equal intervals on the surface of the magnetic shielding cylinder 801, including an interval between respective ends thereof. With the present embodiment, twelve units of the roller assemblies 805 are provided. With this structure, the magnetic shielding door 802a is supported by the wheels on the outer side of the respective roller assemblies 805, and the magnetic shielding door 802b is supported by the wheels on the inner side of the respective roller assemblies 805. The magnetic shielding doors 802a, 802b can be smoothly shifted along the wheels of the respective roller assemblies 805 while in rotation around the y-axis.

Further, with the use of the roller assemblies 805 made of the electrically conductive material, the respective roller assemblies 805 come into electrical contact with the magnetic shielding cylinder 801, and the magnetic shielding doors 802a, 802b, respectively, so that it becomes possible to attain electrical or magnetic connection between the magnetic shielding cylinder 801, and the magnetic shielding door 802a as well as the magnetic shielding door 802b.

Figure 9A:
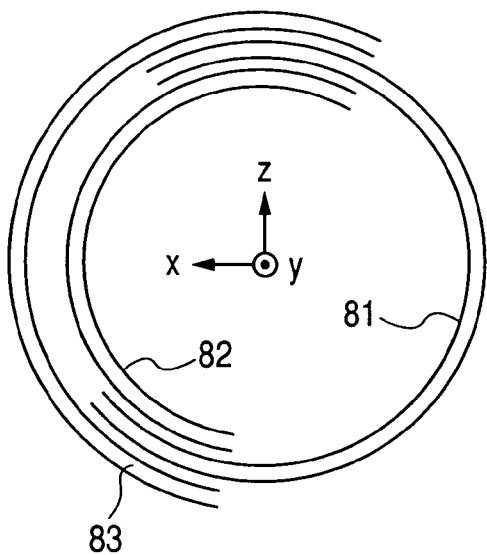
FIG. 9A and FIG. 9B are schematic cross-sectional views showing respective models used in analyses of simulations for evaluation of effects of the invention, FIG. 9C being a graph showing results of the simulations.
Figure 9B:
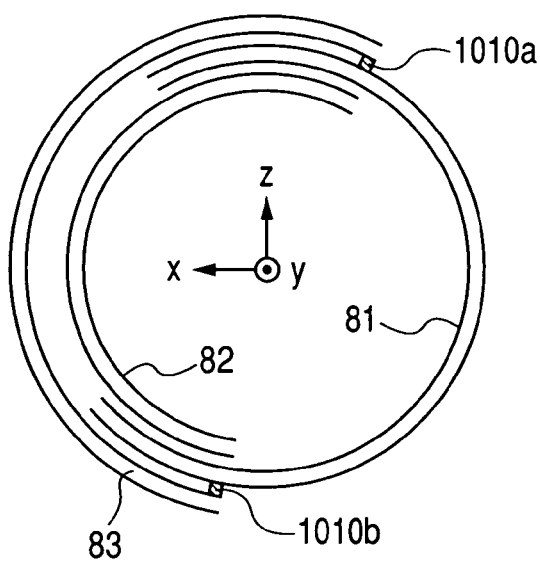
Figure 9C:
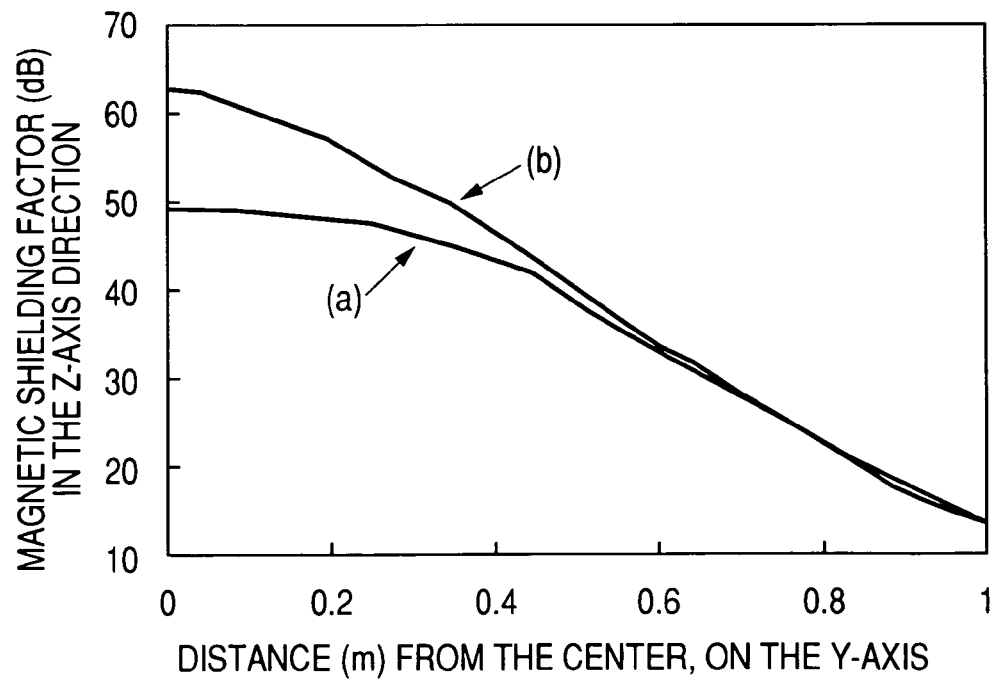

FIGS. 9A and 9B are schematic cross-sectional views showing respective models used in analyses of simulations, conducted for evaluation of effects of the magnetic shielding apparatus according to the embodiments of the invention. FIG. 9C is a graph showing results (distribution of a magnetic shielding factor) obtained from the simulations performed on the respective models shown in FIGS. 9A and 9B, that is, showing distribution of the magnetic field inside the magnetic shielding apparatus as a magnetic shielding factor on the y-axis.

FIG. 9A is a schematic cross-sectional view of the model made up of cylindrical shields 81, 82, and 83, made of a high-permeability material with a relative magnetic permeability at 60,000, each comprising two circumferential parts 200 cm long in the direction of the y-axis, and 1 mm thick. The cylindrical shields 81, 82, 83, each comprise two arc parts having a predetermined angular range, vertical to the center axis, provided at respective ends thereof, two regions, parallel to the center axis, having a predetermined area of a predetermined small width and a predetermined length, and the circumferential parts having a predetermined angular range. The cylindrical shields 82, and 83 each have an identical angular range, and the cylindrical shield 81 has a predetermined angular range differing from those for the cylindrical shields 82, and 83. The cylindrical shield 82 is disposed on the inner side of the cylindrical shield 81 while the cylindrical shield 83 is disposed on the outer side of the cylindrical shield 81.

The cylindrical shield 81 has portions thereof, overlapping the cylindrical shields 82, and 83. The circumferential part of the cylindrical shield 81 is 102 cm in inner diameter, and 114 cm in outer diameter, having the predetermined angular range of 260°. The circumferential part of the cylindrical shield 82 is 94 cm in inner diameter, and 100 cm in outer diameter, having the predetermined angular range of 200°. The circumferential part of the cylindrical shield 83 is 116 cm in inner diameter, and 122 cm in outer diameter, having the predetermined angular range of 200°. The cylindrical shields 82, and 83 are each disposed so as to overlap the cylindrical shield 81 through 60° in the forward region along the z-axis, and through 40° in the backward region along the z-axis.

FIG. 9B shows a variation of the model in FIG. 9A, with electromagnetic connecting members 1010a, 1101b, interposed between the cylindrical shield 81, and the cylindrical shield 83.

The graph in FIG. 9C shows results of tests on distribution of the magnetic shielding factor inside the magnetic shielding apparatus, as found through a simulation by the three-dimensional finite element method in the case of applying a uniform magnetic field in the direction of the z-axis to the models shown in FIGS. 9A and 9B, respectively. The horizontal axis indicates the y-axis of the respective models shown in FIGS. 9A and 9B, and the vertical axis indicates the magnetic shielding factor. Upon comparison of the magnetic shielding factor at the center (y=0) for one of the models with that for the other, it is found that the magnetic shielding factor for the model shown in FIG. 9B is about 62 dB while the magnetic shielding factor for the model shown in FIG. 9A is about 50 dB. Based on the results of the simulation as above, it is evident that the magnetic shielding factor is improved by about 12 dB owing to the effects of the electromagnetic connecting members 1010a, 1101b, interposed between the cylindrical shield 81, and the cylindrical shield 83, verifying that the presence of the electromagnetic connecting members 1010a, 1010b has significantly contributed to improvement of the magnetic shielding factor.

Figure 10:
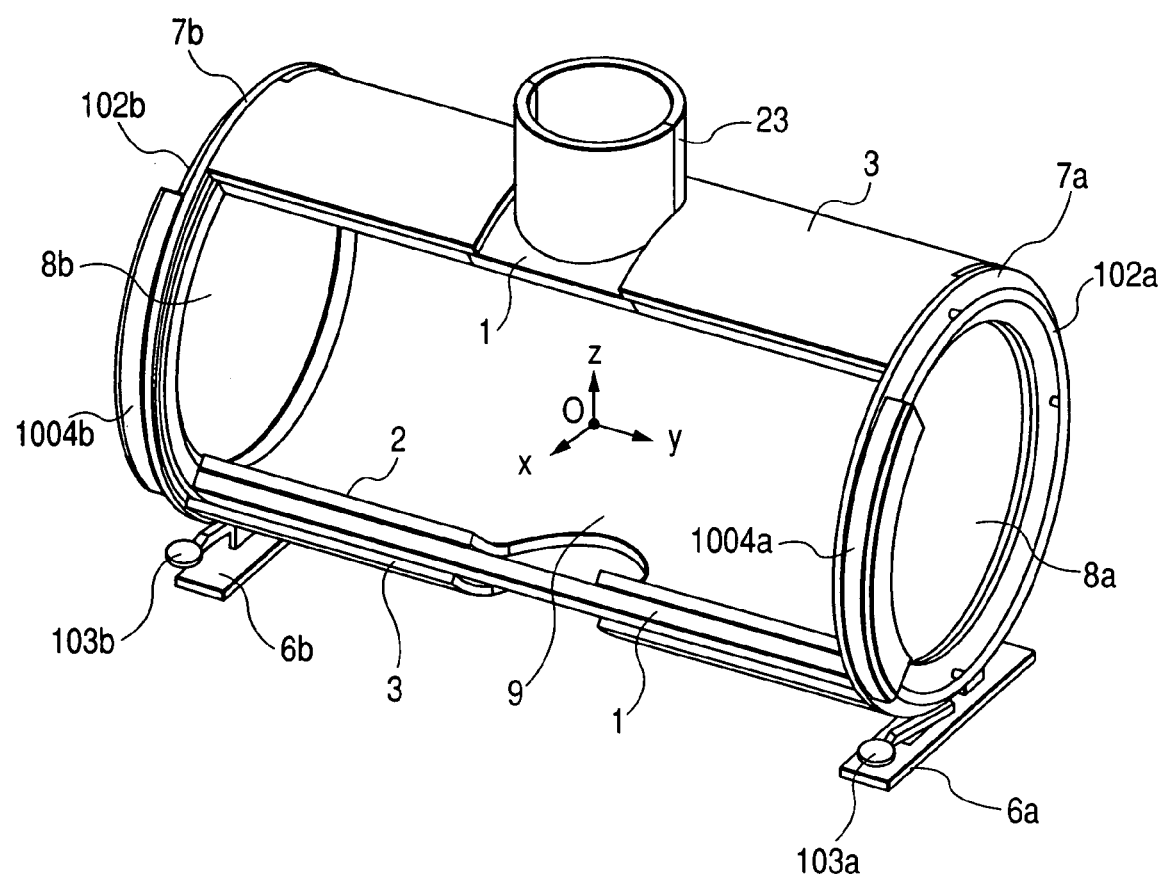
FIG. 10 is a perspective view of a magnetic shielding apparatus according to still another embodiment of the invention.

FIG. 10 is a perspective view of a magnetic shielding apparatus according to still another embodiment of the invention, showing a state where an opening 9 is at the maximum, that is, a state where magnetic shielding doors 2, 3 are in a fully-opened state. The magnetic shielding apparatus shown in FIG. 10 comprises main members including a magnetic shielding cylinder 1 disposed so as to surround the y-axis, the magnetic shielding doors 2, 3, and an auxiliary magnetic shielding cylinder 23. Openings 8a, 8b are provided at respective ends of the magnetic shielding apparatus 1, in the y-axis direction.

The magnetic shielding door 2 is disposed on the inner side of the magnetic shielding cylinder 1, and the magnetic shielding door 3 is disposed on the outer side of the magnetic shielding cylinder 1. The magnetic shielding doors 2, 3 are joined together at respective ends thereof, in the y-axis direction, and the magnetic shielding doors 2, 3, integral with each other, can be shifted along the magnetic shielding cylinder 1 while in rotation around the y-axis.

The magnetic shielding cylinder 1, and the magnetic shielding doors 2, 3 are each made of the high-permeability material, or the highly electrically conductive material. The auxiliary magnetic shielding cylinder 23 is made of the high-permeability material. The magnetic shielding cylinder 1 is joined to, and supported by shield supports 6a, 6b.

Respective ends of the magnetic shielding doors 2, 3, in the forward regions along the y-axis direction, are joined to a rotating part 7a while respective ends of the magnetic shielding doors 2, 3, in the backward regions along the y-axis direction, are joined to a rotating part 7b. The rotating part 7a includes a rotating member, and is rotatably joined to an outer side face of the shield support 6a through the intermediary of the rotating member while the rotating part 7b includes a rotating member, and is rotatably joined to an outer side face of the shield support 6b through the intermediary of the rotating member. For the rotating member, use is made of, for example, a combination of a protrusion of a T-shaped rail and a depression of a U-shaped rail, a pulley, ball bearings, and so froth, made of a nonmagnetic material. The magnetic shielding doors 2, 3 can be shifted in the respective directions of both the arrows in FIG. 1 while in rotation around the y-axis. A rotation handle 102a is joined to the rotating part 7a, and a rotation handle 102b is joined to the rotating part 7b, so that the magnetic shielding doors 2, 3 can be shifted in rotation around the y-axis, respectively, by executing rotational operation of the rotation handle 102a or the rotation handle 102b. Alternatively, a makeup may be adopted such that the magnetic shielding door 2, or 3 is driven in rotation by use of a pneumatic, or an oil hydraulic pump instead of by the rotational operation of the rotation handle 102a or the rotation handle 102b.

In order to facilitate shifting of the magnetic shielding doors 1, and 2, balancers 1004a, 1004b are disposed at the rotating parts 7a, 7b, respectively. Respective weights and positions of the balancers 1004a, 1004b are preferably determined on conditions that balance is achieved between moment of inertia of the balancers 1004a, 1004b and moment of inertia of the magnetic shielding doors 1, 2. More specifically, the magnetic shielding doors 1, 2 preferably come to a standstill at any position, respectively, in a state where no external force is at work.

Further, the magnetic shielding cylinder 1 is electrically or magnetically connected to the magnetic shielding doors 1, 2, respectively, through the intermediary of electromagnetic connecting members made of the highly electrically conductive material although not shown in FIG. 10.

Figure 11:
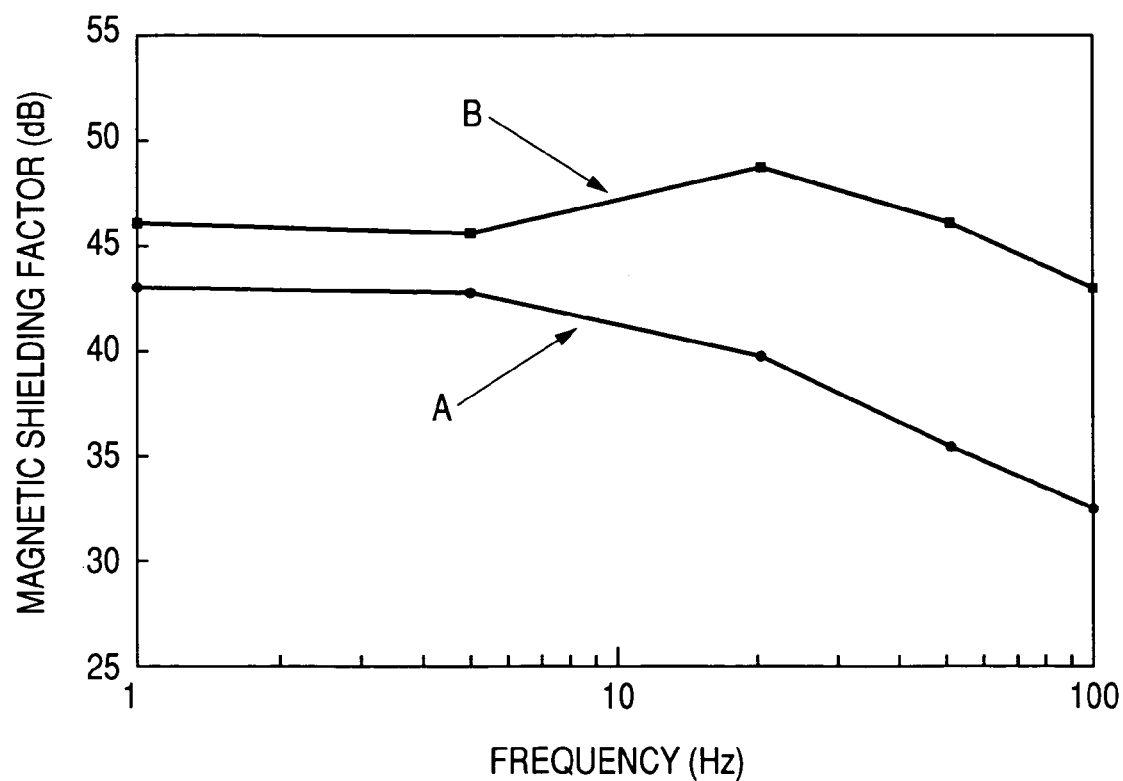
FIG. 11 is a graph showing results of experiments conducted for evaluation of effects of the invention.

FIG. 11 is a graph of results of experiments, showing frequency characteristics of a magnetic shielding factor in the direction of the z-axis of the magnetic shielding apparatus in FIG. 10. The graph shows the results of the experiments, verifying effects of electrical connection. The horizontal axis indicates frequency of an external magnetic field, and the vertical axis indicates the magnetic shielding factor. A curve A indicates the frequency characteristics of the magnetic shielding factor of the magnetic shielding apparatus in FIG.

10 in the case where no electromagnetic connecting member made of the highly electrically conductive material is inserted between the magnetic shielding cylinder 1, and the magnetic shielding doors 2, 3, respectively, while a curve B indicates the frequency characteristics of the magnetic shielding factor of the magnetic shielding apparatus in FIG. 10 in the case where the electromagnetic connecting member made of the highly electrically conductive material is inserted between the magnetic shielding cylinder 1, and the magnetic shielding doors 2, 3, respectively.

In a frequency range of 1 to 10 Hz, the curve B shows that the magnetic shielding factor was found at about 46 dB in contrast to the curve A showing that the magnetic shielding factor was found at about 43 dB. At 20 Hz in frequency, the curve B shows that the magnetic shielding factor was found at about 48 dB in contrast to the curve A showing that the magnetic shielding factor was found at about 40 dB. The results show that in a frequency range of 20 to 100 Hz, as well, the magnetic shielding factor according to the curve B was found higher by about 8 dB in comparison with that for the curve A. On the basis of the results of the experiments, it is evident that the magnetic shielding factor is improved by from about 3 to about 8 dB owing to the effects of the electromagnetic connecting members inserted between the magnetic shielding cylinder 1, and the magnetic shielding doors 2, 3, respectively, and electromagnetic connection between the magnetic shielding cylinder 1, and the magnetic shielding doors 2, 3, respectively, has significantly contributed to improvement of the magnetic shielding factor.

Figure 12:
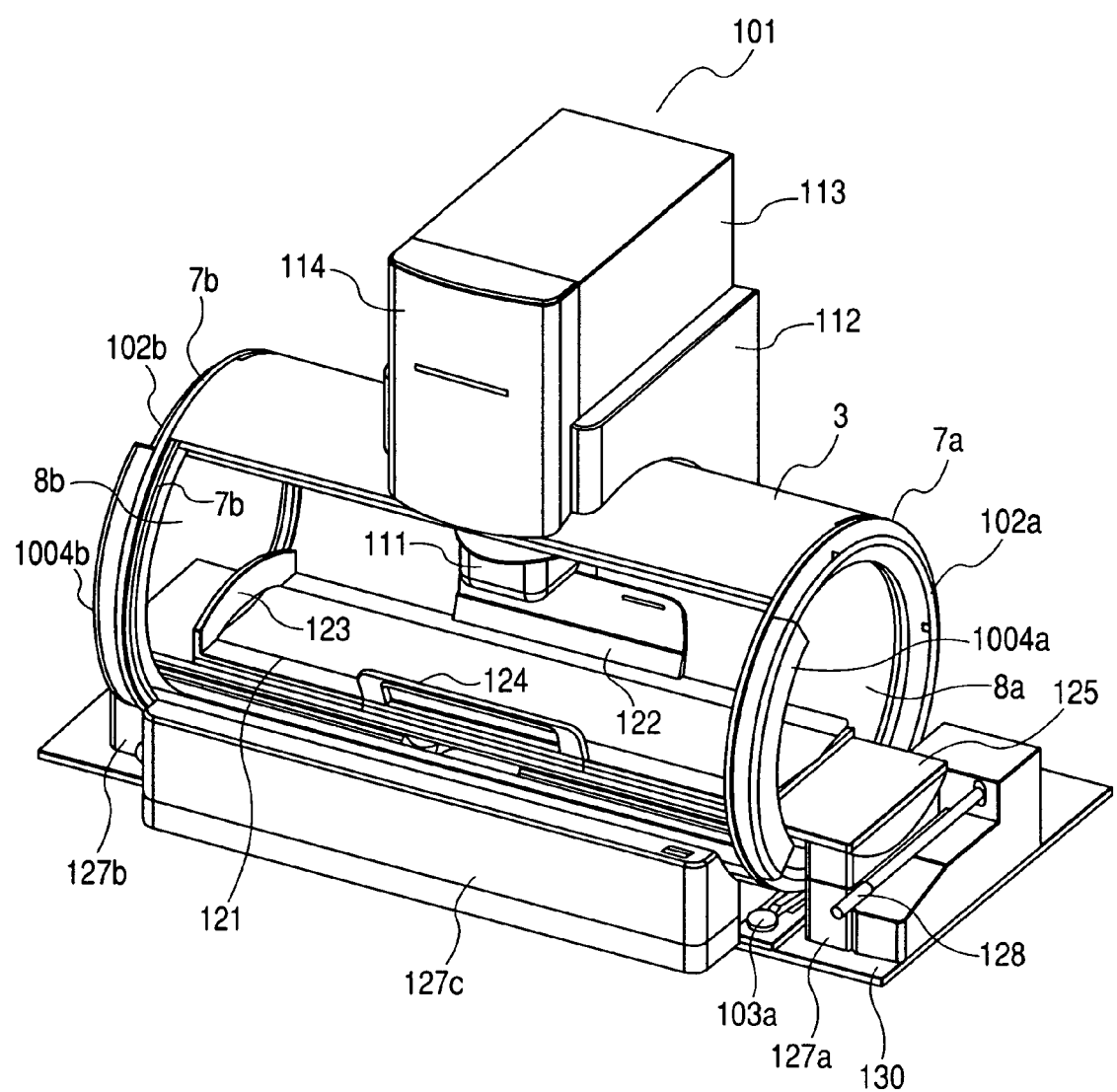
FIG. 12 is a perspective view of a biomagnetism measuring apparatus according to one embodiment of the invention.

FIG. 12 is a perspective view showing a makeup of principal parts of a biomagnetism measuring apparatus according to an embodiment of the invention, showing magnetic shielding doors 2, 3 of a magnetic shielding apparatus, in a fully-opened state.

Figure 14:
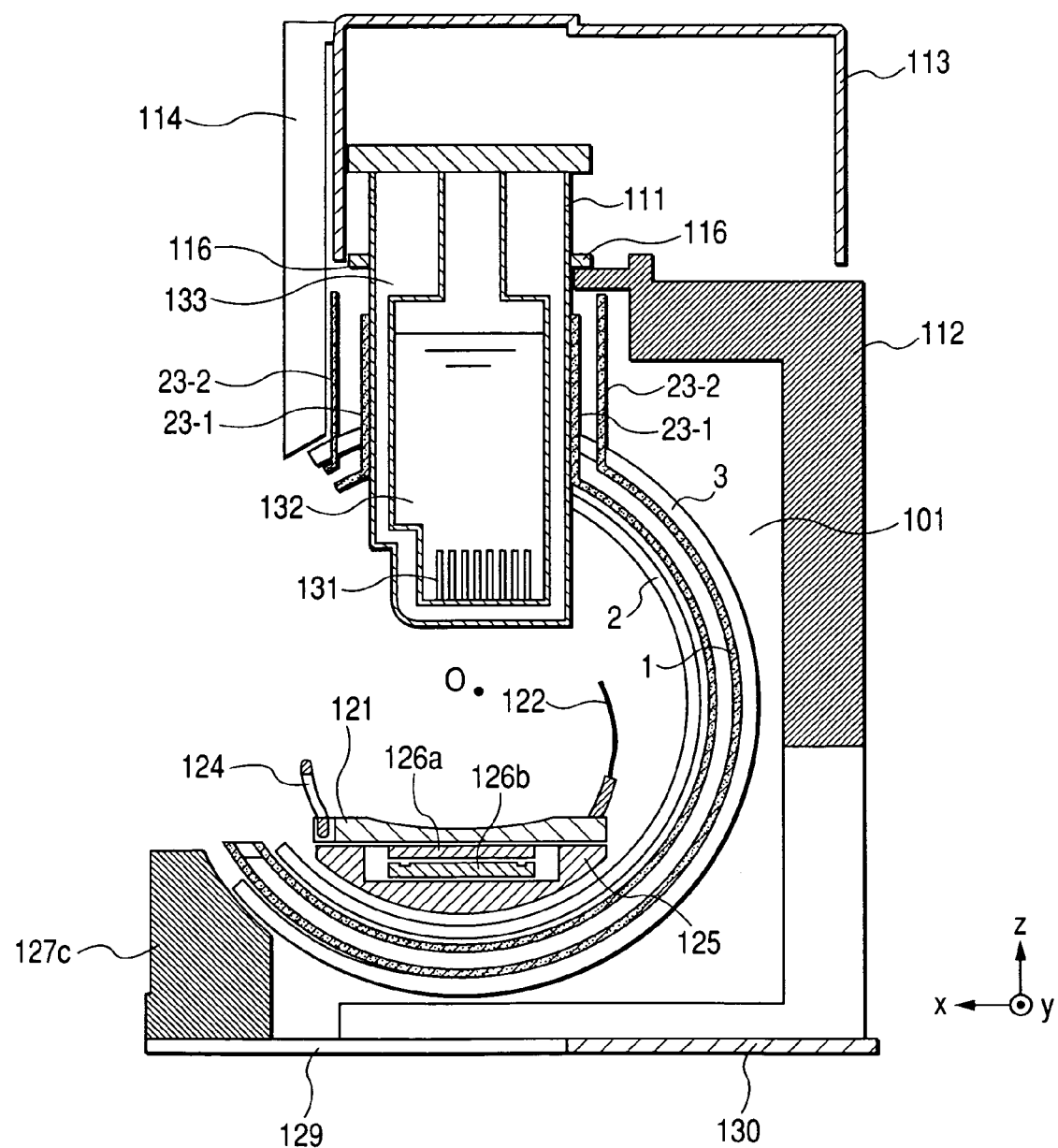
FIG. 14 is a sectional view of the biomagnetism measuring apparatus shown in FIG. 12, taken along a z-x plane.

FIG. 13 is a sectional view of the biomagnetism measuring apparatus shown in FIG. 12, taken along a y-z plane. FIG. 14 is a sectional view of the biomagnetism measuring apparatus shown in FIG. 12, taken along a z-x plane.

In FIGS. 13 and 14, there are shown mutual positional relationship of auxiliary magnetic shielding cylinders 23-1, 23-2, disposed in two layers, respectively, a magnetic shielding cylinder 1, magnetic shielding doors 2, 3, a cryostat 111, a plurality of SQUID flux meters 131, a gantry 112, a top board 121, elements 126a, 126b, 125, 127a, 127b, 127c, used for shifting the top board 121 in the respective directions of the x, y, and z axes, and so forth, and respective structures thereof.

The biomagnetism measuring apparatus in FIG. 12 comprises in broad terms a magnetic shielding part, cryostat part, gantry part, and bed part, as shown in FIG. 12, and a SQUID drive circuit, processor (computer), display monitor, and input unit, as not shown in FIG. 12. Further, elements that are not shown in FIG. 12 will be shown in FIG. 16, which is referred to later, to be then described in detail.

The magnetic shielding part comprises a magnetic shielding apparatus 101 identical in makeup to the magnetic shielding apparatus in FIG. 10. Rotation handles 102a, 102b, to be used for opening and closing of the magnetic shielding doors 2, 3, respectively, are joined to the magnetic shielding doors 2, 3, shown in FIG. 10, respectively, and the magnetic shielding doors 2 or 3 can be opened and closed by manual rotation of the rotation handles 102a, or 102b, thereby varying a spread of the opening 9.

Locking of the magnetic shielding door 2 or 3 can be easily tuned ON/OFF by an operation for pedaling either a locking mechanism 103a or a locking mechanism 103b for the magnetic shielding door 2 or 3.

Further, a pneumatic, or an oil hydraulic pump is controlled by an operation lever 128 disposed on a top board receptacle platform 127c, so that adjustment of a position of a top board holder platform 125 for holding the top board 121, in the direction of the z-axis, can be easily executed. By use of the pneumatic, or the oil hydraulic pump, or so forth, as controlled by a rotational operation button (not shown) disposed on the top board receptacle platform 127c, the magnetic shielding doors 2, 3 are driven in rotation to thereby enable opening/closing of the magnetic shielding door 2 or 3 to be controlled with ease. In addition, by use of a shift operation button (not shown) of a top board shift part disposed on the top board receptacle platform 127c, it is possible to control shifting within a plane parallel to an x-y plane of the top board 121.

Accordingly, the inspection engineer can control adjustment of the position of the top board 121, and the opening/closing of the magnetic shielding door 2 or 3 at a position in front of the magnetic shielding apparatus by selective use of the rotational operation button, operation lever, and shift operation button as necessary while observing the inspection target, so that the inspection target will not have insecure feeling. Obviously, it is also possible for the inspection engineer at the position in front of the magnetic shielding apparatus to manually control the adjustment of the position of the top board 121, and the opening/closing of the magnetic shielding door 2 or 3 while observing the inspection target. The cryostat part holds the cryostat 111 for keeping a single or the plurality of the SQUID flux meters at a low temperature to be housed in a lower interior part thereof. The cryostat 111 is preferably made of a nonmagnetic material (resin for FRP, and so forth).

The gantry part includes the gantry 112 for holding the cryostat 111 of the cryostat part. The gantry part is preferably made of a nonmagnetic material (aluminum, SUS, and so forth). The cryostat 111 is fixedly attached to gantry support platforms 112a, 112b, and the gantry support platforms 112a, 112b are fixedly attached to a bed part support plate 130. An arc-shaped part for accommodating a collar 116 formed on an upper part of the peripheral surface of the cryostat 111 is formed above the gantry 112.

Upper parts of the gantry 112, and the cryostat 111, respectively, are protected by an upper cover 131, and the fronts of the gantry 112, and the cryostat 111, respectively are protected by a front cover 114. The upper cover 131 and the front cover 114 are preferably made of a high-permeability material (Permalloy, and so forth) or a highly electrically conductive material (aluminum, and so forth). The upper cover 131 and the front cover 114 have a function of shielding not only a leakage magnetic field, but also electromagnetic waves at radio frequency, causing the performance of the SQUID flux meters to be deteriorated.

The bed part comprises the top board 121 used for placing the inspection target thereon, the top board holder platform 125 for holding the top board 121, the top board shift part for holding the top board 121 to be shifted within the plane parallel to the x-y plane, the top board holder platform shift part 127a, 127b, (not seen in the perspective view in FIG. 12, but shown in the perspective view in FIG. 13 showing the makeup of the bed part) for holding the top board holder platform 125 to be shifted in the direction of the z-axis, and the top board receptacle platform 127c. The bed part is preferably made of a nonmagnetic material (wood, aluminum, SUS, and so forth).

The top board 121 is provided with a proximal end fence 124, a distal end fence 122, on respective sides of the top board 121, corresponding to the hands of the inspection target, and a fence 123 on a side of the top board 121, corresponding to the legs of the inspection target. The fences 122, 124 are disposed in such a way as to prevent the inspection target from lying off the top board 121 in the direction of the x-axis. The fence 123 is disposed in such a way as to prevent the legs of the inspection target from lying off the top board 121 in the direction of the y-axis. The top board holder platform 125 is disposed inside the magnetic shielding apparatus 101 in such a way as to penetrate through the openings 8a, 8b, provided at respective ends of the magnetic shielding apparatus, in the direction of the y-axis, and is held by the top board holder platform shift part 127a, 127b, disposed outside of the magnetic shielding apparatus 101.

The top board shift part includes top board shift plates 126a, 126b, and elements used for holding the top board 121 to be shifted within the plane parallel to the x-y plane. The elements include a combination of protrusions of T-shaped rails and depressions of U-shaped rails, pulleys, ball bearings, and so froth, made of a nonmagnetic material. Shifting of the top board 121, within the plane parallel to the x-y plane, is executed by automatic control using the shift operation button of the top board shift part disposed on the top board receptacle platform 127c, or by a manual operation for shifting the top board 121. The top board 121 is held by the top board shift plate 126a disposed on the back surface side of the top board 121, and can be shifted in the direction of the x-axis within the plane parallel to the x-y plane, relative to the top board shift plate 126a. The protrusions of the T-shaped rails disposed on the back surface of the top board 121, running in the direction of the x-axis, are inserted into the depressions of the U-shaped rails disposed on the top board shift plate 126a, running in the direction of the x-axis, respectively.

The top board shift plate 126a can be shifted in the direction of the y-axis within the plane parallel to the x-y plane, relative to the top board shift plate 126b. The top board shift plate 126a is held by the top board shift plate 126b through the intermediary of a combination of protrusions of T-shaped rails and depressions of U-shaped rails, pulleys, ball bearings, and so froth.

The top board shift plate 126a can be shifted in the direction of the x-axis within the plane parallel to the x-y plane, relative to top board holder platform 125. Respective ends of the top board shift plate 126b, in the direction of the y-axis, are inserted into depressions of U-shaped rails formed on the inner walls of a concave part extended in the direction of the y-axis, formed in the x-y plane of the top board holder platform 125, parallel to x-z planes at respective ends of the concave part, in the direction of the y-axis.

Shifting of the top board 121, in the direction of the z-axis, is controlled by the operation lever 128 disposed on the top board receptacle platform 127c, disposed on the proximal end of the magnetic shielding apparatus 101. The top board holder platform shift part 127a, 127b are housed in respective depressions provided in the bed part support plate 130 to be held thereby. The respective depressions provided in the bed part support plate 130 are not shown in FIG. 12, but are shown in FIGS. 13, and 14. The top board holder platform shift part 127a, 127b each include a pneumatic or an oil hydraulic pump made of a nonmagnetic material (aluminum, SUS, and so forth). The pneumatic or the oil hydraulic pump is controlled by the operation lever 128.

The magnetic shielding apparatus, the bed part, and the gantry part are each disposed independently from each other so as not to allow a load to be mutually applied thereto. The load of the magnetic shielding apparatus is supported by the shield supports 6a, 6b, the load of the bed part is supported by the top board holder platform shift part 127a, 127b and the load of the gantry part is supported by the gantry support platforms 112a, 112b.

The bed part is held by the bed part support plate 130. Further, the top board holder platform shift part 127a, 127b, the top board receptacle platform 127c, and the gantry 112 joined to the gantry support platforms 112a, 112b are held by the bed part support plate 130. The locking mechanism 103a or 103b, disposed in the forward or backward region, in the y-axis direction, is held on the proximal end side of the bed part support plate 130. Further, a carriage insertion port 129 for enabling a lower part (not shown) of a transport carriage (not shown) for transporting the cryostat 111 held at an optional height to be inserted under the bed part is formed on the proximal end side of the bed part support plate 130. Detailed explanation on the shift mechanism of the top board 121, in the respective directions of the x, y, and z-axes, and a rotation mechanism for the magnetic shielding doors 2, 3 will be described later.

Figure 15A:
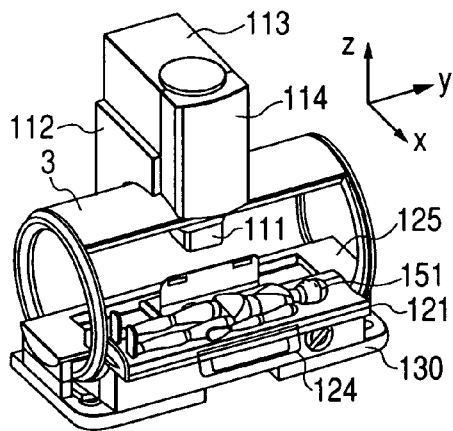
FIG. 15A, FIG. 15B, FIG. 15C, FIG. 15D, FIG. 15E, and FIG. 15F are perspective views for describing a procedure of measuring a magnetic field of the heart with the use of the biomagnetism measuring apparatus shown in FIG. 12.
Figure 15D:
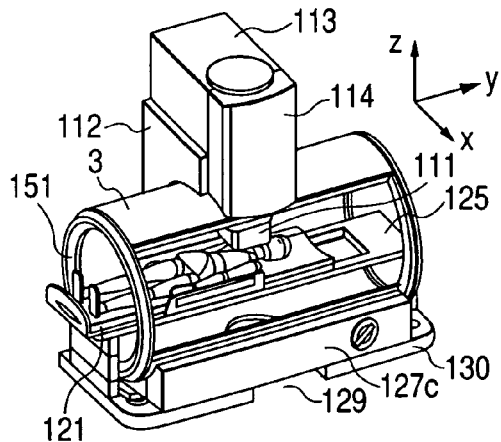
Figure 15B:
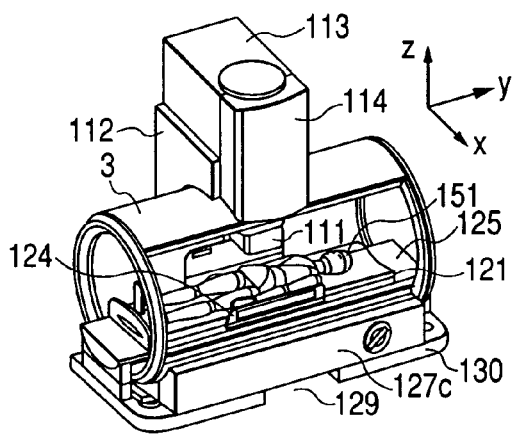
Figure 15E:
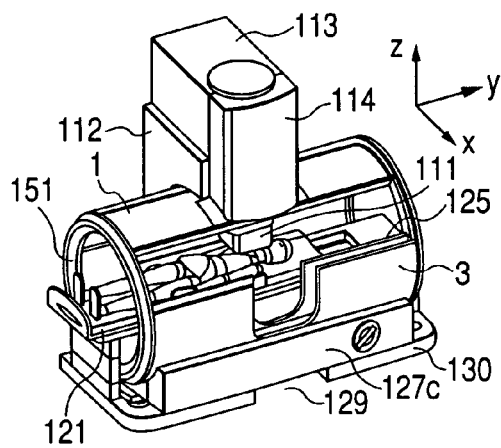
Figure 15C:
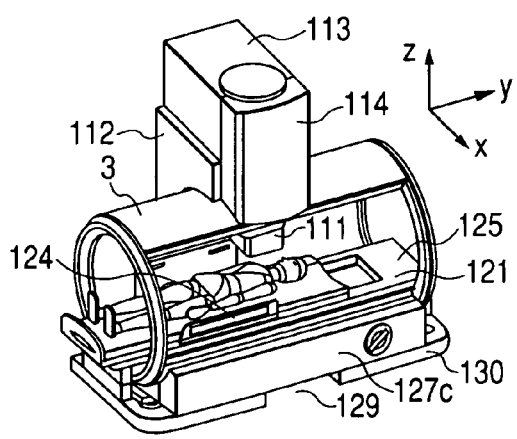
Figure 15F:
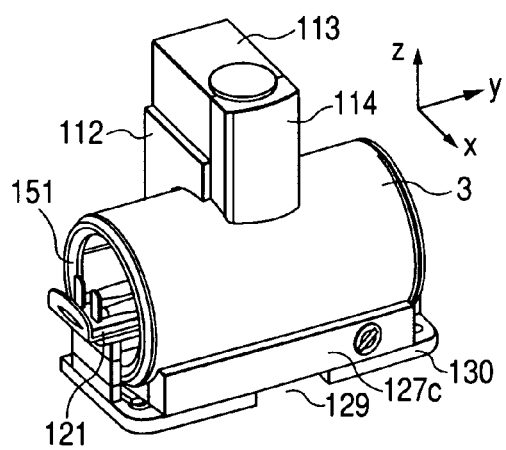

FIGS. 15A to 15F are perspective views for describing a procedure of measuring a magnetic field of the heart with the use of the biomagnetism measuring apparatus shown in FIG. 12. FIGS. 15A to 15D each show the magnetic shielding doors 2, 3, in a fully-opened state (refer to FIG. 3), and FIG. 15E shows the magnetic shielding doors 2, 3, in a half-opened state, FIG. 15F showing the magnetic shielding doors 2, 3, in a completely-closed state.

First, the top board 121 is pulled out in the forward direction along the x-axis so as to be placed outside of the magnetic shielding apparatus, as shown in FIG. 15A, and after locking the top board 121 so as to be at rest, the fence 124 is folded before laying down an inspection target 151 on the top board 121. At this point in time, the inspection target 151 is caused to take a supine posture such that the body axis of the inspection target becomes substantially parallel to the y-axis. Also, the inspection target 151 is placed such that the feet of the inspection target point toward the fence 123. The reason for doing so is because there is a tendency of the feet rather than the head of the inspection target 151 lying off the top board 121 if the inspection target 151 is tall, and by doing so, it is possible to eliminate the risk of the feet coming into collision with the magnetic shielding apparatus, in particular, with the rotating part 7b (refer to FIGS. 12, 13) thereof, when inserting the top board 121 into the magnetic shielding part.

In a stage where the inspection target 151 has taken the supine posture on the top board 121 as shown in FIG. 15A, the fence 124 is erected and the top board 121 is disengaged from locking, whereupon the top board 121 is shifted in the backward direction along the x-axis to be inserted into the interior of the magnetic shielding apparatus, and positioning of the top board 121, in the x-axis direction, is carried out. After completion of the positioning of the top board 121, in the x-axis direction, the top board 121 is shifted in the y-axis direction, thereby executing positioning of the top board 121, in the y-axis direction. FIG. 15C shows a state of completion of the positioning of the top board 121, in the directions of the x-axis, and y-axis, respectively. After the completion of the positioning of the top board 121, in the directions of the x-axis, and y-axis, respectively, the top board 121 is caused to move upward or downward in the direction of the z-axis with the use of the operation lever 128 to thereby bring the surface of the breast of the inspection target close to the bottom of the cryostat 111. FIG. 15D shows a state of completion of the positioning of the top board 121, in three directions of the x, y, and z-axes, respectively.

The positioning of the top board 121, in the respective directions of the x, y, and z-axes, is carried out by visual check only, by visual identification using one light source (not shown) emitting linear laser light, two light sources (not shown) emitting sector laser light, and laser marker affixed to the surface of the body of the inspection target, or by optical and/or electrical automatic identification.

After the completion of the positioning of the top board 121, in the three directions of the x, y, and z-axes, respectively, the rotation handle 102a or the rotation handle 102b is rotated to thereby turn the magnetic shielding doors 2, 3 from the fully-opened state to the half-opened state to observe a condition of the inspection target, and upon the magnetic shielding doors 2, 3 being turned in the completely-closed state, the magnetic shielding doors 2, 3 are locked manually or automatically, as shown in FIGS. 15D to 15F. In that state, measurement of the magnetic field of the heart is started.

After completion of the measurement of the magnetic field of the heart, the magnetic shielding doors 2, 3 are disengaged from locking by means of the locking mechanisms 103a and 103b, respectively, to thereby turn the magnetic shielding doors 2, 3 into the fully-opened state (the state shown in FIG. 15C), the top board 121 is slowly moved downward in the z-axis direction to be subsequently shifted in the y-axis direction so as to revert to the state shown in FIG. 15B, the top board 121 is subsequently pulled out in the forward direction along the x-axis so as to revert to the state shown in FIG. 15A, the top board 121 is locked so as to be at rest, and the fence 124 is then folded before having the inspection target 151 unloaded from the top board 121, thereby completing a series of the steps of the measurement.

Figure 16:
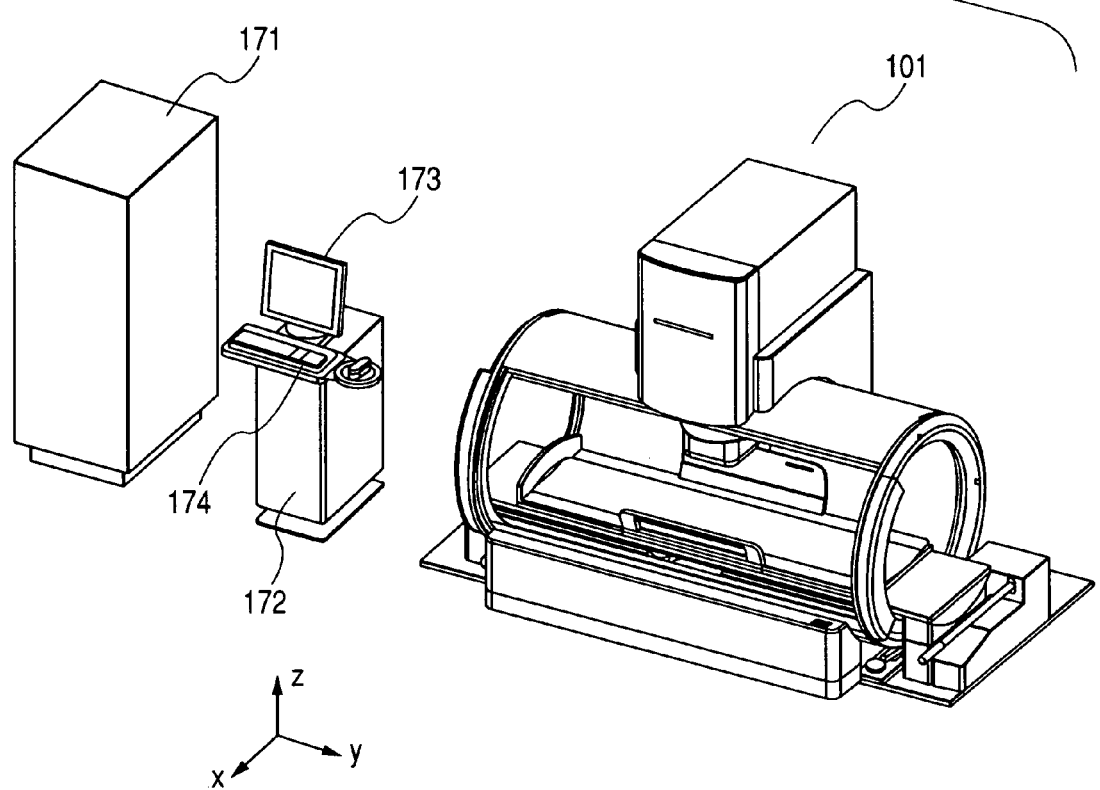
FIG. 16 is a perspective view showing the whole makeup of the biomagnetism measuring apparatus according to the embodiment of the invention.

FIG. 16 is a perspective view showing the whole makeup of the biomagnetism measuring apparatus according to the embodiment of the invention. In FIG. 16, there is shown the magnetic shielding apparatus with the magnetic shielding doors 2, 3, in a fully-opened state, as with the case of those in FIG. 12. FIG. 16 shows the whole makeup of the biomagnetism measuring apparatus wherein a SQUID drive circuit 171, processor (computer) 172, display monitor 173, and input unit 174 are connected to the biomagnetism measuring apparatus 101 shown in FIG. 12. It is to be pointed out, however, that wire connections between respective components including the biomagnetism measuring apparatus 101, SQUID drive circuit 171, processor (computer) 172, display monitor 173, and input unit 174 are not shown in FIG. 16 for clarity and simplification.

A single, or a plurality of the SQUID flux meters 131 are driven for control by the SQUID drive circuit 171. Magnetic field signals detected by the SQUID flux meters 131 are collected in a memory of the processor 172 as digital signals to be subsequently analyzed by the processor 172. Results of analysis are displayed on the display monitor 173. Parameters inputted from the input unit 174 can vary drive parameters for the SQUID drive circuit 171, or the content of a screen for displaying an output on the display monitor 173.

Figure 17:
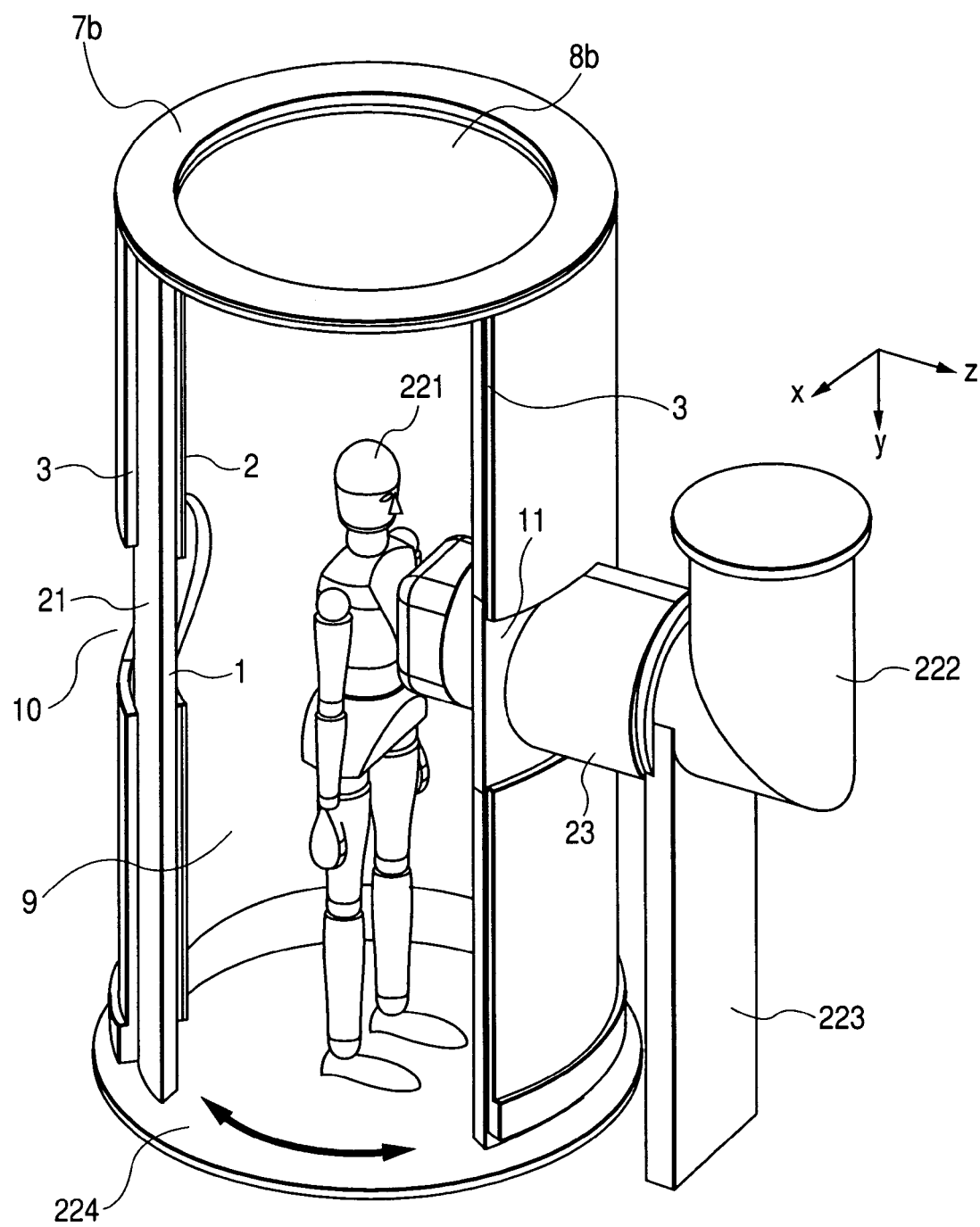
FIG. 17 is a perspective view showing the makeup of principal parts of a biomagnetism measuring apparatus according to another embodiment of the invention.

FIG. 17 is a perspective view showing the makeup of principal parts of a biomagnetism measuring apparatus according to another embodiment of the invention. With the magnetic shielding apparatus shown in FIG. 10, the center axis thereof is oriented in the horizontal direction however, with the magnetic shielding apparatus shown in FIG. 17, the center axis thereof is oriented in the vertical direction. More specifically, with the biomagnetism measuring apparatus using the magnetic shielding apparatus shown in FIG. 10, measurements are performed on an inspection target in a supine posture or a prone posture; however, with the magnetic shielding apparatus shown in FIG. 17, measurements are performed on an inspection target in a standing posture or a sitting posture. In the case of the makeup shown in FIG. 17, magnetic shielding doors 2, 3, integral with each other, can be shifted in respective directions of both arrows while in rotation around the y-axis. In FIG. 17, there is shown a state where the magnetic shielding doors 2, 3 are half-open in the respective directions of both the arrows. Further, the magnetic shielding apparatus described hereinafter with reference to FIG. 17 is substantially the same in dimension as the magnetic shielding apparatus in FIG. 10 as previously described.

The biomagnetism measuring apparatus shown in FIG. 17 largely differs from the biomagnetism measuring apparatus shown in FIG. 12 mainly in respect of points including a point that the center axis of the magnetic shielding apparatus is oriented in the vertical direction (the horizontal direction in FIG. 12), a point that a bed is not used (the bed is used in FIG. 12), a point that a L-shaped cryostat 222 is used (the cryostat 111 of a linear type is used in FIG. 12), a point that a measurement plane is along the vertical plane (along the horizontal plane in FIG. 12), a point that the magnetic shielding doors 2, 3 are rotated from side to side (rotated upward and downward in FIG. 12), and so forth.

In spite of such points of difference as described above, the magnetic shielding apparatus of the bio-magnetism measuring apparatus shown in FIG. 17 is substantially the same in makeup as the magnetic shielding apparatus shown in FIG. 10. However, in FIG. 17, the weight of magnetic shielding apparatus is supported by a support plate 224 in place of the shield supports 6a, 6b shown in FIG. 10. The L-shaped cryostat 222 for keeping the plurality of the SQUID flux meters arranged on a plane parallel to the x-y plane at a low temperature is supported by an L-shaped gantry 223.

The gantry 223 is fixedly attached to a floor surface. An opening 20 through which the L-shaped cryostat 222 is inserted is provided with an auxiliary magnetic shielding cylinder 23 to thereby shield an ambient magnetic field otherwise intruding into the magnetic shielding apparatus.

A multi-layer auxiliary magnetic shielding cylinder may be substituted for the auxiliary magnetic shielding cylinder 23 in one layer. Auxiliary magnetic shielding cylinders in two layers 23-1, 23-2 can also be used in place of the auxiliary magnetic shielding cylinder 23.

Cutouts each with a planar region, oriented in at least four directions, are formed in regions of an end face of the L-shaped cryostat 222, adjacent to a plane facing the inspection target. More specifically, there are formed at least the cutouts in two parts opposite to each other (respective parts in the forward and backward regions in the y-axis direction), in the direction parallel to the center axis of the magnetic shielding apparatus, and the cutouts in two parts opposite to each other (respective parts in the forward and backward regions in the x-axis direction), in the direction orthogonal to the center axis of the auxiliary magnetic shielding cylinder 23 as well as the center axis of the magnetic shielding apparatus.

The cutouts oriented in the four directions (each with the planar region) are formed in order to increase a volume of a refrigerant contained in the L-shaped cryostat 222 as much as possible while giving a consideration so as not to cause the inspection target to suffer feeling of oppression.

The measurement of the magnetic field of the heart is executed after the breast of the inspection target 221 in a standing posture is brought close to the end face of the L-shaped cryostat 222 to be then at rest. The magnetic shielding doors 2, 3, integral with each other, are closed at the time of executing the measurement of the magnetic field of the heart, as with the cases of the magnetic shielding apparatuses shown in FIG. 4, and FIG. 15F, respectively. With the magnetic shielding apparatus shown in FIG. 17, measurements on the inspection target 221 in the standing posture can be carried out, so that there is an advantageous effect in that an area occupied by the magnetic shielding apparatus can be smaller than that for the magnetic shielding apparatus shown in FIG. 15F.

Further, in the case of the measurements shown in FIG. 17, since the top board 121 is not used, there is no need for the shift mechanism of the top board 121, in the respective directions of the x, y, and z-axes. Further, in FIG. 17, the rotation mechanism for the magnetic shielding doors 2, 3 are not shown in detail; however, the same rotation mechanism as the rotation mechanism for use in the magnetic shielding apparatus of the biomagnetism measuring apparatus shown in FIG. 12 is applicable.

Furthermore, in FIG. 17, use can be made of a chair at which the inspection target 221 sits, and also, a shift mechanism for shifting the chair in the respective directions of the x, y, and z-axes as well as a rotation/shift mechanism for shifting the chair in rotation around an axis parallel to the-y axis can be used. The support plate 224 may be expanded in area to permit the gantry 223 to be fixedly attached to the support plate 224. The support plate 224 and the gantry 223 may be fixedly attached to a metal plate, and the metal plate may be placed on the floor surface so as to disperse pressure.

With the embodiments described hereinbefore, the measurement of the magnetic field of the heart has been explained by way of example, however, the biomagnetism measuring apparatus according to the embodiments of the invention can be applied to measurement of a magnetic field generated from the brains of the inspection target, due to activities of cerebral nerves (hereinafter referred to as a brain magnetic field), and measurement of a magnetic field generated from the heart of a fetus inside a parent body, and a brain magnetic field thereof. Further, with the embodiments described above, a cylinder whose cross-section orthogonal to the center axis thereof is circular is adopted by way example for the auxiliary magnetic shielding cylinder 23, 23-1, 23-2, the magnetic shielding cylinder 1, and the magnetic shielding doors 2, 3, respectively, however, a cylinder whose cross-section is in the shape of an ellipse, an oval, or a polygon having four sides, six sides, eight sides, and so forth may be adopted instead.

Still further, the bed part support plate 130 shown in FIGS. 12, 13, and 14, respectively, may be fixedly attached to a metal plate, or a metal plate large in thickness may be used for the bed part support plate 130, and the metal plate may be then placed on the floor surface so as to disperse pressure.

Yet further, with the embodiments described in the foregoing, the SQUID flux meter is used for a magneto-metric sensor used in the measurement of biomagnetism by way example, however, use may be made of any of other magneto metric sensors, such as a magneto resistive element, a giant magneto resistive element, a flux-gate flux meter, an optically pumped magnetometer, and so forth.

According to the embodiments of the invention, it is possible to enhance a magnetic shielding factor against a leakage magnetic field, and to implement a cylindrical magnetic shielding apparatus small in size and light in weight, having a high magnetic shielding factor, thereby enabling a biomagnetism measuring apparatus capable of performing accurate measurement with higher sensitivity to be implemented, and enabling restrictive conditions required for installation of the biomagnetism measuring apparatus to be alleviated.

Thus, the invention can provide a cylindrical magnetic shielding apparatus with an enhanced magnetic shielding factor against a leakage magnetic field, so that with the invention, a biomagnetism measuring apparatus capable of performing accurate measurement with higher sensitivity can be implemented.

What is claimed is:

1. A magnetic shielding apparatus comprising:
   a magnetic shielding cylinder made of a high-permeability material, having an opening, and disposed so as to surround one axis;
   a magnetic shielding door made of a high-permeability material, for opening and closing the opening; and
   electromagnetic connecting members for electromagnetically connecting the magnetic shielding cylinder to the magnetic shielding door with the opening in a closed state due to rotational shifting of the magnetic shielding door in a direction of the one axis, said magnetic shielding apparatus being configured to shield a component of an external magnetic field, in a direction vertical to the one axis, wherein the electromagnetic connecting members have control members that touch the magnetic shielding door at the time of stopping rotational shifting of the magnetic shielding door and that do not touch the magnetic shielding door at a time of the rotational shifting of the magnetic shielding door.

2. A magnetic shielding apparatus according to claim 1, wherein the electromagnetic connecting members are electrically conductive members and/or high-permeability members.

3. A magnetic shielding apparatus according to claim 2, wherein the electrically conductive members and/or high-permeability members have flexibility.

4. A magnetic shielding apparatus according to claim 2, wherein the electrically conductive members are made of copper or aluminum.

5. A magnetic shielding apparatus comprising:
   first and second nonmagnetic cylindrical members having circumferential parts of first and second predetermined angular ranges, respectively, formed by disposing a plurality of high-permeability members having a high-permeability so as to partially overlap each other, and to concentrically surround one axis;
   means for fixedly attaching the first cylindrical member to a floor surface substantially vertical to the one axis;
   means for rotating the second cylindrical member around the one axis; and
   balancers for assisting rotation of the second cylindrical member, wherein
   the first cylindrical member and the second cylindrical member overlap each other for a third predetermined angular range at respective ends thereof, in a direction parallel to the one axis, due to rotation of the second cylindrical member, to thereby shield a component of an external magnetic field in a direction vertical to the one axis, to be split in two in the circumferential direction,
   the first cylindrical member being in a state of being closed in the circumferential direction upon the first cylindrical member and the second cylindrical member overlapping each other for the third predetermined angular range,
   said magnetic shielding apparatus further comprising electromagnetic connecting members for electromagnetically connecting between respective portions of the first cylindrical member and the second cylindrical member, overlapping each other, upon the first cylindrical member being in the state of being closed, and
   the electromagnetic connecting members have control members that touch the second cylinder member at a time of stopping rotation of the second cylindrical member, and that do not touch the second cylindrical member at the time of rotating the second cylindrical member.

6. A magnetic shielding apparatus according to claim 5, wherein the electromagnetic connecting members are electrically conductive members and/or high-permeability members.

7. A magnetic shielding apparatus according to claim 6, wherein the electrically conductive members and/or high-permeability members have flexibility.

8. A magnetic shielding apparatus according to claim 6, wherein the electrically conductive members are made of copper or aluminum.

9. A magnetic field measuring apparatus comprising:

a magnetic shielding apparatus that comprises a magnetic shielding cylinder made of a high-permeability material, having an opening, and disposed so as to surround one axis, a magnetic shielding door made of a high-permeability material, for opening and closing the opening, and electromagnetic connecting members for electromagnetically connecting the magnetic shielding cylinder to the magnetic shielding door with the opening in a closed state due to rotational shifting of the magnetic shielding door in a direction of the one axis, wherein the electromagnetic connecting members have control members that touch the magnetic shielding door at a time of stopping rotational shifting of the magnetic shielding door, and that do not touch the magnetic shielding door at the time of rotating the magnetic shielding door, said magnetic shielding apparatus being configured to shield a component of an external magnetic field, in a direction vertical to the one axis;

means for holding a living body with a direction of the body axis thereof, kept substantially parallel to the one axis inside the magnetic shielding apparatus; and a magnetometric sensor for detecting a component of a magnetic field generated from the living body, in a direction vertical to the one axis.

10. A magnetic field measuring apparatus according to claim 9, wherein the electromagnetic connecting members are electrically conductive members and/or high-permeability members.

11. A magnetic field measuring apparatus according to claim 10, wherein the electrically conductive members and/or high-permeability members have flexibility.

12. A magnetic field measuring apparatus according to claim 10, wherein the electrically conductive members are made of copper or aluminum.

* * * * *